US010743762B2

United States Patent
Shimizu et al.

(10) Patent No.: US 10,743,762 B2
(45) Date of Patent: Aug. 18, 2020

(54) OPHTHALMOLOGIC APPARATUS

(71) Applicant: TOPCON CORPORATION, Tokyo (JP)

(72) Inventors: Hitoshi Shimizu, Tokyo (JP); Masashi Nakajima, Ageo (JP); Tony H. Ko, Milpitas, CA (US); Jonathan Liu, Tokyo (JP); Yasufumi Fukuma, Wako (JP)

(73) Assignee: TOPCON CORPORATION, Tokyo (JP)

( * ) Notice: Subject to any disclaimer, the term of this patent is extended or adjusted under 35 U.S.C. 154(b) by 204 days.

(21) Appl. No.: 16/146,144

(22) Filed: Sep. 28, 2018

(65) Prior Publication Data

US 2020/0100673 A1    Apr. 2, 2020

(51) Int. Cl.
*A61B 3/14*    (2006.01)
*A61B 3/00*    (2006.01)
(Continued)

(52) U.S. Cl.
CPC .......... *A61B 3/1225* (2013.01); *A61B 3/0025* (2013.01); *A61B 3/0058* (2013.01);
(Continued)

(58) Field of Classification Search
CPC ......... A61B 3/102; A61B 3/14; A61B 5/0066; A61B 3/0025; A61B 3/12; A61B 3/1233; A61B 5/0261; A61B 3/1241; A61B 3/1225; A61B 5/026; A61B 5/0285; A61B 5/489; A61B 3/0091; A61B 5/6821; A61B 5/7278; A61B 5/742; A61B 5/746; A61B 3/103; A61B 3/0058; A61B 3/0083; A61B 3/10;
(Continued)

(56) References Cited

U.S. PATENT DOCUMENTS

2010/0302508 A1\* 12/2010 Yamamoto ......... G01B 9/02044
351/206
2015/0085252 A1    3/2015 Fujimura et al.
(Continued)

FOREIGN PATENT DOCUMENTS

JP    H8-275921    10/1996
JP    2013-248376    12/2013
JP    2016-043155    4/2016

*Primary Examiner* — Brandi N Thomas
(74) *Attorney, Agent, or Firm* — Xsensus LLP

(57) ABSTRACT

An ophthalmologic apparatus according to the embodiments includes an OCT optical system, an alignment unit, an image forming unit, a first calculator, and a second calculator. The OCT optical system is configured to acquire OCT data of a fundus of a subject's eye by projecting measurement light onto the fundus. The alignment unit is configured to perform alignment of the OCT optical system with reference to a predetermined site of the subject's eye. The image forming unit is configured to form a tomographic image of the fundus based on the OCT data acquired by the OCT optical system which has been aligned by the alignment unit. The first calculator is configured to calculate a first tilt angle of the tomographic image. The second calculator is configured to calculate a second tilt angle of the fundus by correcting the first tilt angle based on alignment result of the OCT optical system with respect to the predetermined site by the alignment unit.

17 Claims, 13 Drawing Sheets

(51) Int. Cl.
*A61B 3/12* (2006.01)
*A61B 3/10* (2006.01)

(52) U.S. Cl.
CPC ............ *A61B 3/0083* (2013.01); *A61B 3/102* (2013.01); *A61B 3/1005* (2013.01); *A61B 3/14* (2013.01)

(58) Field of Classification Search
CPC ..... A61B 3/1005; A61B 3/1015; A61B 3/107; A61B 3/117; A61B 3/0008; A61B 3/0041; A61B 3/0075; A61B 3/1025; A61B 3/125; A61B 3/152; A61B 5/0068
USPC ........ 351/200, 205–206, 209–211, 221–223, 351/243–246
See application file for complete search history.

(56) References Cited

U.S. PATENT DOCUMENTS

2015/0313466 A1* 11/2015 Yoshida ................. A61B 5/743
600/425
2016/0345822 A1 12/2016 Fujimura et al.

* cited by examiner

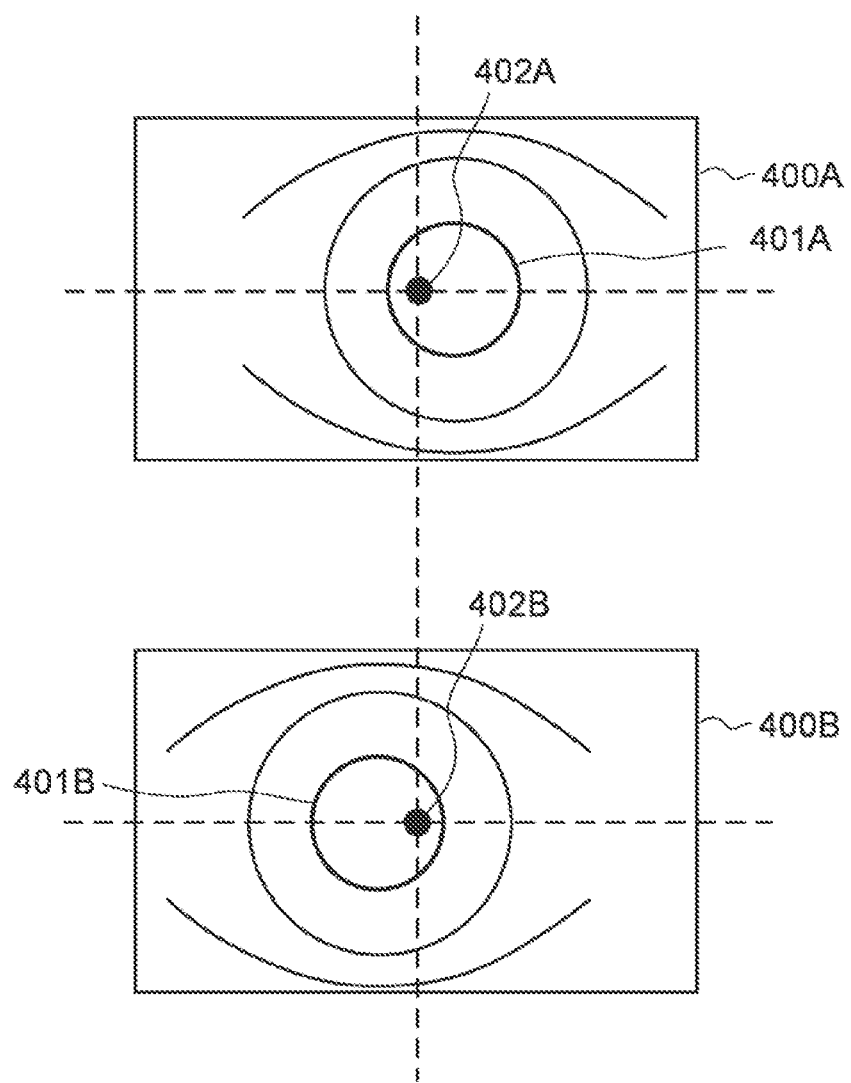

us 10,743,762 B2

OPHTHALMOLOGIC APPARATUS

FIELD

Embodiments according to present invention described herein relate to an ophthalmologic apparatus.

BACKGROUND

Types of ophthalmologic apparatuses include ophthalmologic imaging apparatuses for obtaining images of a subject's eye and ophthalmologic measuring apparatuses for measuring characteristics of a subject's eye.

Examples of the ophthalmologic imaging apparatus include an optical coherence tomography (OCT) apparatus for capturing a tomographic image by using OCT, a fundus camera for photographing the fundus, a scanning laser ophthalmoscope (SLO) for capturing an image of the fundus by laser scanning with the use of a confocal optical system, and the like.

Examples of the ophthalmologic measuring apparatuses include an eye refraction test apparatus (refractometer, keratometer) for measuring the refractive properties of the subject's eye, a tonometer, a specular microscope for obtaining the properties of the cornea (corneal thickness, cell distribution, etc.), a wavefront analyzer for obtaining the aberration information of the subject's eye by using a Hartmann-Shack sensor, and the like.

Regarding ophthalmologic examinations, in terms of precision and accuracy of examinations, position adjustment between the optical system of the apparatus and a subject's eve is very important. This position adjustment is referred to as alignment. Alignment includes the action of aligning the optical axis of the optical system of the apparatus with respect to the axis of a subject's eye (XY alignment), as well as the action of adjusting the distance between the subject's eye and the optical system of the apparatus (Z alignment).

There are various methods for alignment. As an exemplary method, a method, in which a light beam is projected on the cornea and alignment is performed by detecting its reflection image (Purkinje image), is know (see Japanese Unexamined Patent Application Publication No. 08-275921, for example).

Further, as a method realized in recent years, a method, in which a three-dimensional position of a subject's eye from two or more photographic images obtained by photographing an anterior segment from different directions and both XY alignment and Z alignment are performed based on the three-dimensional position, is known (see Japanese Unexamined Patent Application Publication No. 2013-248376, for example).

SUMMARY

The first aspect according to some embodiments is an ophthalmologic apparatus including: an OCT optical system configured to acquire OCT data of a fundus of a subject's eye by projecting measurement light onto the fundus; an alignment unit configured to perform alignment of the OCT optical system with reference to a predetermined site of the subject's eye; an image forming unit configured to form a tomographic image of the fundus based on the OCT data acquired by the OCT optical system which has been aligned by the alignment unit; a first calculator configured to calculate a first tilt angle of the tomographic image; and a second calculator configured to calculate a second tilt angle of the fundus by correcting the first tilt angle based on alignment result of the OCT optical system with respect to the predetermined site by the alignment unit.

The second aspect according to some embodiments is the ophthalmologic apparatus of the first aspect, further including: a misalignment amount specifying unit configured to specify a misalignment amount between a measurement optical axis of the OCT optical system which has been aligned by the alignment unit and an eyeball optical axis of the subject's eye, wherein the second calculator calculates the second tilt angle based on the misalignment amount.

The third aspect according to some embodiments is the ophthalmologic apparatus of the second aspect, wherein the second calculator outputs the first tilt angle as the second tilt angle when the measurement optical axis substantially coincides with the eyeball optical axis.

The fourth aspect according to some embodiments is the ophthalmologic apparatus of the second aspect or the third aspect, wherein the misalignment amount specifying unit specifies, as a shift amount, a displacement amount of the eyeball optical axis with respect to the measurement optical axis in a direction intersecting the measurement optical axis, and the second calculator calculates the second tilt angle by correcting the first tilt angle based on the shift amount, when the eyeball optical axis is shifted with respect to the measurement optical axis.

The fifth aspect according to some embodiments is the ophthalmologic apparatus of the fourth aspect, wherein the second calculator calculates the second tilt angle by correcting the first tilt angle according to a linear expression with the shift amount as variable.

The sixth aspect according to some embodiments is the ophthalmologic apparatus of any one of the second aspect to the fifth aspect, wherein the misalignment amount specifying unit specifies, as a tilt amount, an angle formed by the eyeball optical axis with respect to the measurement optical axis, and the second calculator calculates the second tilt angle by correcting the first tilt angle based on the tilt amount, when the eyeball optical axis is tilted with respect to the measurement optical axis.

The seventh aspect according to some embodiments is the ophthalmologic apparatus of the sixth aspect, wherein the second calculator calculates the second tilt angle by correcting the first tilt angle according to a linear expression with the tilt amount as variable.

The eighth aspect according to sonic embodiments is the ophthalmologic apparatus of the second aspect or the third aspect, wherein the misalignment amount specifying unit specifies, as a shift amount, a displacement amount of the eyeball optical axis with respect to the measurement optical axis in a direction intersecting the measurement optical axis, and specifies, as a tilt amount, an angle formed by the eyeball optical axis with respect to the measurement optical axis, and the second calculator calculates the second tilt angle by correcting the first tilt angle based on the shift amount and the tilt amount, when the eyeball optical axis is shifted and tilted with respect to the measurement optical axis.

The ninth aspect according to some embodiments is the ophthalmologic apparatus of the eighth aspect, wherein the second calculator calculates the second tilt angle by correcting the first tilt angle according to a combining expression obtained by linearly combined a linear expression with the shift amount as variable and a linear expression with the tilt amount as variable.

The tenth aspect according to some embodiments is the ophthalmologic apparatus of any one of the second aspect to the ninth aspect, further including: a fixation projection system configured to project a fixation flux onto the fundus in acquiring the OCT data, wherein the eyeball optical axis is a visual axis.

The eleventh aspect according to sonic embodiments is the ophthalmologic apparatus of any one of the first aspect to the tenth aspect, wherein the alignment unit includes: an alignment light projection system configured to project alignment light onto the subject's eye; a movement mechanism configured to move relatively the subject's eye and the OCT optical system; two or more imaging units configured to photograph an anterior segment of the subject's eye, onto which the alignment light is being projected, from different directions; and a position determination unit configured to specify a first position of a reflection image of a cornea by the alignment light and a second position of the predetermined site by analyzing two or more photographic images obtained by the two or more imaging units, and to determine a movement target position of the OCT optical system based on the first position and the second position.

The twelfth aspect according to some embodiments is the ophthalmologic apparatus of any one of the first aspect to the eleventh aspect, wherein when a value, which is obtained by converting a difference of a distance in a vertical direction between an image region of a site corresponding to a predetermined layer region of the fundus at a right end of a frame of the tomographic image and an image region of the site at a left end of the frame into a value corresponding to an actual dimension, is d and a value, which is obtained by converting a distance in a horizontal direction of the frame of the tomographic image into a value corresponding to an actual dimension, is c, the first calculator calculates the first tilt angle by obtaining arctan (|d|/c).

The thirteenth aspect according to some embodiments is the ophthalmologic apparatus of the twelfth aspect, further including: a conical shape measurement unit configured to perform measurement of at least a corneal curvature radius of the subject's eye; an eye refractometry unit configured to perform measurement of an eye refractive power of the subject's eye; and an intraocular distance calculator configured to calculate an axial length of the subject's eye based on the OCT data, wherein the first calculator converts the distance of the frame of the tomographic image in the horizontal direction into the actual dimension based on the corneal curvature radius, the eye refractive power, and the axial length.

The fourteenth aspect according to sonic embodiments is the ophthalmologic apparatus of the twelfth aspect, further including: a corneal shape measurement unit configured to perform measurement of at least a corneal curvature radius of the subject's eye; and an intraocular distance calculator configured to calculate an axial length of the subject's eye based on the OCT data, wherein the OCT optical system includes a focusing lens that is movable along the measurement optical axis, and the first calculator converts the distance of the frame of the tomographic image in the horizontal direction into the actual dimension based on the corneal curvature radius, a position of the focusing lens on the measurement optical axis, and the axial length.

The fifteenth aspect according to some embodiments is the ophthalmologic apparatus of any one of the twelfth aspect to the fourteenth aspect, wherein the first calculator converts the difference of the distance into the actual dimension by multiplying the difference of the distance by a predetermined pixel spacing value.

The sixteenth aspect according to sonic embodiments is the ophthalmologic apparatus of any one of the first aspect to the fifteenth aspect, further including: a storage unit that stores the second tilt angle calculated by the second calculator in association with information representing acquisition timing of the OCT data; and a controller that controls a display means to display information representing a change over time of the second tilt angle based on the second tilt angle and the information representing the acquisition timing stored in the storage unit.

The seventeenth aspect according to some embodiments is the ophthalmologic apparatus of any one of the first aspect to the fifteenth aspect, further including: a controller that controls a display means to display information representing a reference range of a tilt angle of the fundus so as to be superimposed on the tomographic image formed by the image forming unit.

It should be noted that the configurations according to a plurality of aspects described above can be combined arbitrarily.

BRIEF DESCRIPTION OF THE DRAWINGS

FIG. 8 is a schematic diagram for explaining an operation of the ophthalmologic apparatus of the embodiments.

DETAILED DESCRIPTION

Figure 1:
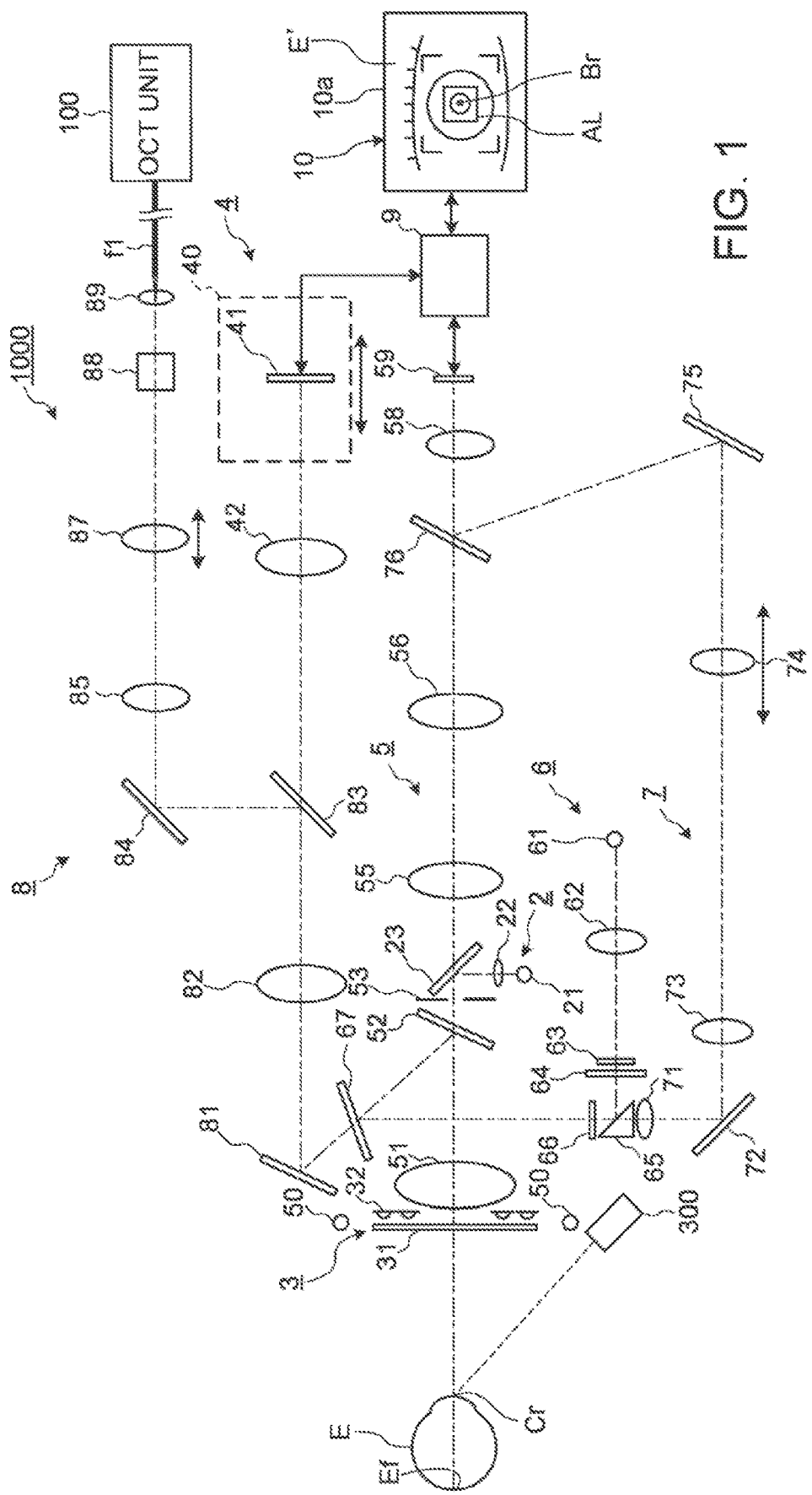
FIG. 1 is a schematic diagram illustrating an example of a configuration of an optical system of an ophthalmologic apparatus according to embodiments.

Some eye diseases such as pathologic myopia are pointed out to be related to the shape of the posterior of the eyeball, or the like. However, in tomographic images obtained by performing OCT measurement on the fundus in the conventional ophthalmologic apparatus, the tilt of the fundus changes according to the state of position adjustment between the optical system of the apparatus and a subject's eye. Therefore, it is difficult to specify whether the tilt of the fundus in the tomographic image is caused by the state of position adjustment or truly due to the deformation of the posterior of the eyeball.

According to some embodiments of the present invention, an ophthalmologic apparatus which is capable of measuring tilt angle of a fundus of a subject's eye with high accuracy can be provided.

Referring now to the drawings, exemplary embodiments of an ophthalmologic apparatus according to the present invention are described below. Any of the contents of the documents cited in the present specification and arbitrary known techniques may be applied to the embodiments below.

An ophthalmologic apparatus according to the embodiments is capable of performing alignment between an optical system of the apparatus and a subject's eye. The ophthalmologic apparatus acquires a tomographic image of the subject's eye by performing OCT measurement after the alignment is completed, obtains a tilt angle of the acquired tomographic image, and calculates a tilt angle of the fundus by correcting the tilt angle of the tomographic image according to the alignment information (misalignment amount) in performing OCT.

Further, the ophthalmologic apparatus according to the embodiments is capable of performing a corneal shape measurement (keratometry), an eye refractometry (refractometry), and a measurement and imaging using OCT.

Hereinafter, the case of using the method of swept source type OCT in the measurement using OCT or the like will be described in detail in the embodiments. However, the configuration according to the embodiments can be applied to ophthalmologic apparatus using another type OCT (for example, the spectral domain type).

An ophthalmologic apparatus according to some embodiments further includes a subjective inspection optical system for perform subjective inspection and an objective measurement system for performing other objective measurement.

The subjective inspection is a method for measurement to acquire information using the responses from the subject. Examples of the subjective inspections include a visual field test, and subjective refractivity measurement such as a far vision test, a near vision test, a contrast test, a glare test and the like.

The objective measurement is a method for measurement to acquire information on the subject's eye mainly by the use of a physical method without referring to the responses from the subject. The objective measurements include a measurement for acquiring the characteristics of the subject's eye and an imaging for acquiring an image of the subject's eye. Examples of the other objective measurements include a tonometry, a fundus photography, and the like.

Hereinafter, a fundus conjugate position is a position substantially optically conjugate with a fundus of a subject's eye in a state where alignment is completed, and means a position optically conjugate with the fundus of the subject's eye or the vicinity of the position. Similarly, a pupil conjugate position is a position substantially optically conjugate with a pupil of a subject's eye in a state where alignment is completed, and means a position optically conjugate with the pupil of the subject's eye or the vicinity of the position.

<Configuration of the Optical System>

FIG. 1 illustrates an example of the configuration of an optical system of the ophthalmologic apparatus according to the embodiments. The ophthalmologic apparatus 1000 according to the embodiments includes an optical system for observing the subject's eye E, an optical system for inspecting the subject's eye E, and a dichroic mirror that wavelength-separates the optical paths of these optical systems. An anterior segment observation (imaging) system 5 is provided as the optical system for observing the subject's eye E. An OCT optical system, a refractometry optical system (refractive power measurement optical system), and the like are provided as the optical system for inspecting the subject's eye E.

The ophthalmologic apparatus 1000 includes an alignment light projection system 2, a keratometry system 3, a fixation projection system 4, the anterior segment observation system 5, a refractometry projection system 6, a refractometry light reception system 7, and an OCT optical system 8. Hereinafter, for example, it is assumed that light with 940 nm to 1000 nm is mainly used in the anterior segment observation system 5, light with 830 nm to 880 nm is used in the refractometry optical system (refractometry projection system 6, refractometry light reception system 7), light with 400 nm to 700 nm is used in the fixation projection system 4, and light with 1000 nm to 1100 nm is used in the OCT optical system 8.

(Anterior Segment Observation System 5)

The anterior segment observation system s is configured to acquire a moving image of an anterior segment of the subject's eye E. In an optical system passing through the anterior segment observation system 5, an imaging plane of an imaging element 59 is arranged at the pupil conjugate position. An anterior segment illumination light source 50 projects illumination light (for example, infrared light) onto the anterior segment of the subject's eye E. The light reflected from the anterior segment of the subject's eve E passes through an objective lens 51, penetrates a dichroic mirror 52, passes through the aperture part formed in a diaphragm (telecentric diaphragm) 53, penetrates a half mirror 23, passes through relay lenses 55 and 56, and penetrates a dichroic mirror 76. The dichroic mirror 52 combines (or separates) the optical path of the refractometry optical system with the optical path of the anterior segment optical system 5. The dichroic mirror 52 is disposed so that its optical path combining surface for combining these optical paths is inclined with respect to the optical axis of the objective lens 51. The light penetrating the dichroic mirror 76 forms an image on an imaging surface of the imaging element 59 (area sensor) by an imaging lens 58. The imaging element 59 performs an imaging and a signal outputting at a predetermined rate. The output (video signal) of the imaging element 59 is input to the processing unit 9. The processing unit 9 displays an anterior segment image E' based on this video signal on a display screen 10a of a display unit 10. The anterior segment image E' is an infrared moving image for example.

(Alignment Light Projection System 2)

The alignment light projection system 2 is configured to project light (infrared light) for performing alignment in an optical axis direction of the anterior segment observation system 5 (i.e., front-back direction, Z direction) and directions orthogonal to the optical axis left-right directions (X direction), up-down directions (Y direction)) onto the subject's eye E. The alignment light projection system 2 includes an alignment light source 21 and a collimator lens 22 that are provided in an optical path branched from the optical path of the anterior segment observation system 5 by the half mirror 23. The light emitted from the alignment light source 21 passes through the collimator lens 22, is reflected by the half mirror 23 and is projected onto the subject's eye E through the anterior segment observation system 5. Reflected light from the cornea Cr of the subject's eye E is guided to the imaging element 59 through the anterior segment observation system 5.

An image (bright spot image) Br of the reflected light is included in the anterior segment image E'. The processing unit 9 controls the display unit to display an alignment mark AL and the anterior segment image E' including the bright spot image Br on the display screen of the display unit. In the case of performing XY alignment manually, a user can perform an operation for moving the optical system so as to guide the bright spot image Br in the alignment mark AL. In the case of performing Z alignment manually, a user can perform the operation for movement of the optical system while referring to the anterior segment image E' displayed on the display screen of the display unit. In the case of performing alignment automatically, the processing unit 9 controls a mechanism for moving the optical system so as to satisfy a predetermined alignment completion condition based on a position of a predetermined site (for example, pupil center position) of the subject's eye E and a position of the bright spot image Br, described after.

(Keratometry System 3)

The keratometry system 3 is configured to project a ring-shaped light flux (infrared light) for measuring a shape of the cornea Cr of the subject's eye E onto the cornea Cr. A kerato board 31 is disposed between the objective lens 51 and the subject's eye E. A kerato-ring light source 32 is provided on the back side (the objective lens 51 side) of the kerato board 31. By illuminating the kerato board 31 with light from the kerato-ring light source 32, the ring-shaped light flux (arc-like or circular measurement pattern) is projected onto the cornea Cr. The reflected light (kerato-ring image) from the cornea Cr of the subject's eye E is detected by the imaging element 59 along with the anterior segment image E'. The processing unit 9 calculates a corneal shape parameter representing a shape of the cornea Cr, by performing a known calculation based on this kerato-ring image.

(Refractometry Projection System 6 and Refractometry Light Reception System 7)

The refractometry optical system includes the refractometry projection system 6 and the refractometry light reception system 7 which are used for eye refractive power measurement. The refractometry projection system 6 is configured to project light flux (a ring-shaped light flux, for example) (infrared light) for measuring eye refractive power onto the fundus Ef. The refractometry light reception system 7 is configured to receive returning light of the light flux from the subject's eye E. The refractometry projection system 6 is provided in an optical path branched by the perforated prism 65 provided in an optical path of the refractometry light reception system 7. A hole part formed in the perforated prism 65 is arranged at the pupil conjugate position. In the optical system passing through the refractometry light reception system 7, an imaging surface of the imaging element 59 is arranged at the fundus conjugate position.

In some embodiments, the refractometry light source 61 is a SLD (Super Luminescent Diode) which is a high-intensity light source. The refractometry light source 61 is movable in the optical axis direction. The refractometry light source 61 is arranged at the fundus conjugate position. The light emitted from the refractometry light source 61 passes through the relay lens 62 and is incident on a conical surface of the conical prism 63. The light incident on the conical surface is deflected and emits from a bottom surface of the conical prism 63. The light emitted from bottom surface of the conical prism 63 passes through a ring-shaped light transmission part formed in a ring diaphragm 64. The light (ring-shaped light flux) passing through the light transmission part of the ring diaphragm 64 is reflected on a reflective surface formed around the hole part of the perforated prism 65, passes through a rotary prism 66, and is reflected by the dichroic mirror 67. The light reflected by the dichroic mirror 67 is reflected by the dichroic mirror 52, passes through the objective lens 51, and is projected onto the fundus Et The rotary prism 66 is used for averaging the light quantity distribution of the ring-shaped light flux with respect to the blood vessel or the diseased site of the fundus Ef or for reducing the speckle noise caused by the light source.

Returning light of the ring-shaped light flux projected onto the fundus Ef passes through the objective lens 51, and is reflected by the dichroic mirrors 52 and 67. The returning light reflected by the dichroic mirror 67 passes through the rotary prism 66, passes through the hole part of the perforated prism 65, passes through a relay lens 71, is reflected by a reflective mirror 72, and passes through a relay lens 73 and a focusing lens 74. The focusing lens 74 is movable along an optical axis of the refractometry light reception system 7. The light passing through the focusing lens 74 is reflected by the reflective mirror 75, is reflected by a half mirror 76, and forms an image on the imaging surface of the imaging element 59 by an imaging lens 58. The processing unit 9 calculates an eye refractive power (eye refractive power value) of the subject's eye E by performing the known calculation based on the output of the imaging element 59. For example, the eye refractive power includes spherical power, degree of astigmatism, and astigmatic axis angle, or equivalent spherical power.

(Fixation Projection System 4)

The OCT optical system 8, which will be described after, is provided in the optical path wavelength-separated from the optical path of the refractometry optical system by the dichroic mirror 67. The fixation projection system 4 is provided in the optical path wavelength-separated from the optical path of the OCT optical system 8 by the dichroic mirror 83.

The fixation projection system 4 is configured to present a fixation target to the subject's eye E. A fixation unit 40 is disposed in the optical path of the fixation projection system 4. The fixation unit 40 is movable along an optical axis of the fixation projection system 4 under the control of the processing unit 9 described after. The fixation unit 40 includes a liquid crystal panel 41.

Under the control of the processing unit 9, the liquid crystal panel 41 displays a pattern representing a fixation target. By changing the display position of the fixation target on the screen of the liquid crystal panel 41, the fixation position of the subject's eye E can be changed. Examples of the fixation position of the subject's eye E include a position for acquiring an image centered at a macular region of the fundus Ef, a position for acquiring an image centered at an optic disc, and a position for acquiring an image centered at the fundus center between the macular region and the optic disc. The display position of the pattern representing the fixation target can be arbitrarily changed. Alternatively, instead of the liquid crystal panel 41, a transmissive visual target chart for refractometry in which a visual target or the like is printed on a film or the like, a light source for illumination for illuminating the visual target chart, and a point light source for OCT measurement may be provided.

The light from the liquid crystal panel 41 passes through a relay lens 42, penetrates a dichroic mirror 83, passes through a relay lens 82, is reflected by a reflective mirror 81, penetrates a dichroic mirror 67, and is reflected by the dichroic mirror 52. The light reflected by the dichroic mirror 52 passes through the objective lens 51 and is projected onto a fundus Ef. In some embodiment, each of the liquid crystal panel 41 and the relay lens 42 is independently movable in the optical axis direction.

Figure 3A:
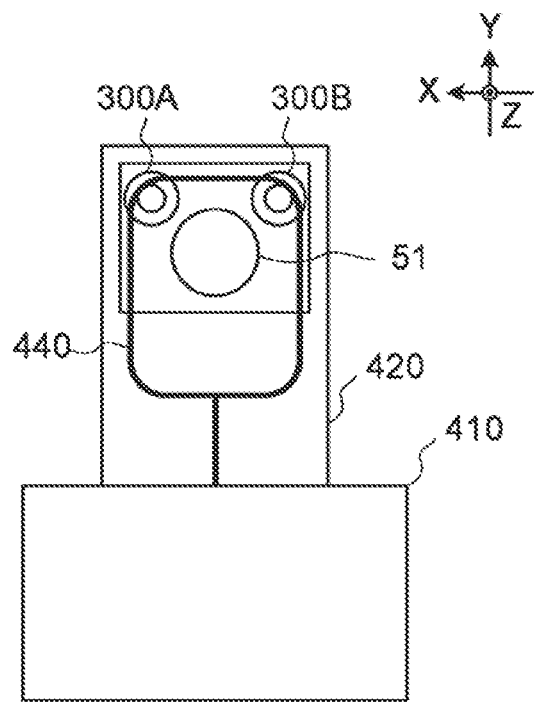
FIG. 3A is a schematic diagram for explaining a configuration of the ophthalmologic apparatus of the embodiments.

The ophthalmologic apparatus 1000 is provided with the anterior segment cameras 300. The anterior segment cameras 300 photograph the anterior segment of the subject's eye E from different directions. In the embodiment, two cameras are provided on the surface of the ophthalmologic apparatus 1000 facing the subject (see anterior segment cameras 300A and 300B in FIG. 3A). The anterior segment cameras 300A and 300B are, as illustrated in FIGS. 1 and 3A, arranged in positions away from the optical axis of the objective lens 51 (optical path (optical axis) of the anterior segment observation system 5, optical path (optical axis) of the OCT optical system 8). In the following, the two anterior segment cameras 300A and 300B may sometimes be collectively represented by reference numeral 300.

Figure 3B:
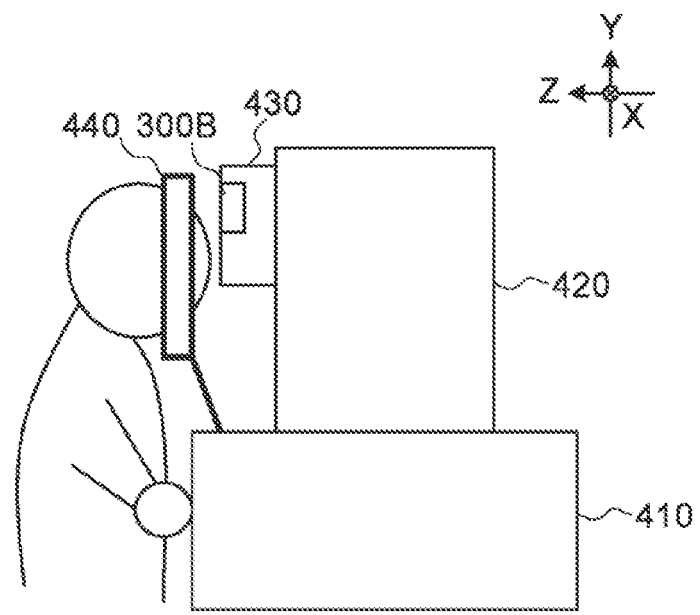
FIG. 3B is a schematic diagram for explaining a configuration of the ophthalmologic apparatus of the embodiments.

FIG. 3A and FIG. 3B show an outline of an external configuration of the ophthalmologic apparatus 1000.

The ophthalmologic apparatus 1000 is provided with a jaw holder and a forehead rest for supporting the face of the subject. The jaw holder and the forehead rest correspond to a supporter 440 illustrated in FIGS. 3A and 3B. The driving system such as a movement mechanism 200 and the processing unit 9 are stored in the base 410. A body 420 that accommodates the optical systems is provided on the base 410. A lens case 430 that accommodates the objective lens 51 is provided on the front surface of the body 420.

In the embodiment, the two anterior segment cameras 300A and 300B are provided; however, the number of anterior segment cameras may be any number more than one.

Moreover, in the embodiment, the anterior segment cameras 300 are separately provided from the anterior segment observation system 5; however, similar anterior-segment photography can be performed using at least the anterior segment observation system 5. In some embodiments, one of the two or more anterior segment cameras includes the anterior segment observation system 5 (imaging element 59). The ophthalmologic apparatus 1000 according to the embodiments may be configured to be able to photograph the anterior segment from two or more different directions.

In some embodiments, at least one anterior segment illumination light source 50 (infrared light source or the like) can be provided in the vicinity of each of the two or more anterior segment cameras. For example, an anterior segment illumination light source provided in the upper vicinity of the anterior segment camera 300A and an anterior segment illumination light source provided in the lower vicinity of the anterior segment camera 300A, and an anterior segment illumination light source provided in the upper vicinity of the anterior segment camera 300B and an anterior segment illumination light source provided in the lower vicinity of the anterior segment camera 300B are provided.

The two or more anterior segment cameras can substantially simultaneously photograph the anterior segment from two or more different directions. The phrase "substantially simultaneously" indicates that the deviation in photography timings at a level where the eye movement is negligible is allowed in the photography with two or more anterior segment cameras. Thereby, images of the subject's eye E located in substantially the same position (orientation) can be acquired by the two or more anterior segment cameras.

The two or more anterior segment cameras may capture still images as well as moving images. In the case of moving image photography, substantially simultaneous photography of the anterior segment as described above can be realized by performing control for synchronizing photography start timings, controlling the frame rates or the capture timings of respective frames, or the like. On the other hand, in the case of still image photography, this can be realized by performing control for synchronizing photography timings.

(OCT Optical System 8)

The OCT optical system 8 shown in FIG. 1 is an optical system for performing OCT measurement. For example, the position of the focusing lens 87 is adjusted so that an end face of an optical fiber f1 and a photographing site (fundus Ef or the anterior segment) are optically conjugate with each other based on the result of the refractometry performed before the OCT measurement. Alternatively, for example, the position of the focusing lens 87 is adjusted so that the intensity of the interference signal obtained in the OCT measurement becomes maximized.

The OCT optical system 8 is provided in the optical path wavelength-separated from the optical path of the refractometry optical system by the dichroic mirror 67. The optical path of the above fixation projection system 4 is coupled with the optical path of the OCT optical system 8 by the dichroic mirror 83. Thereby, the optical axes of the OCT optical system 8 and the fixation projection system 4 can be coupled coaxially.

Figure 2:
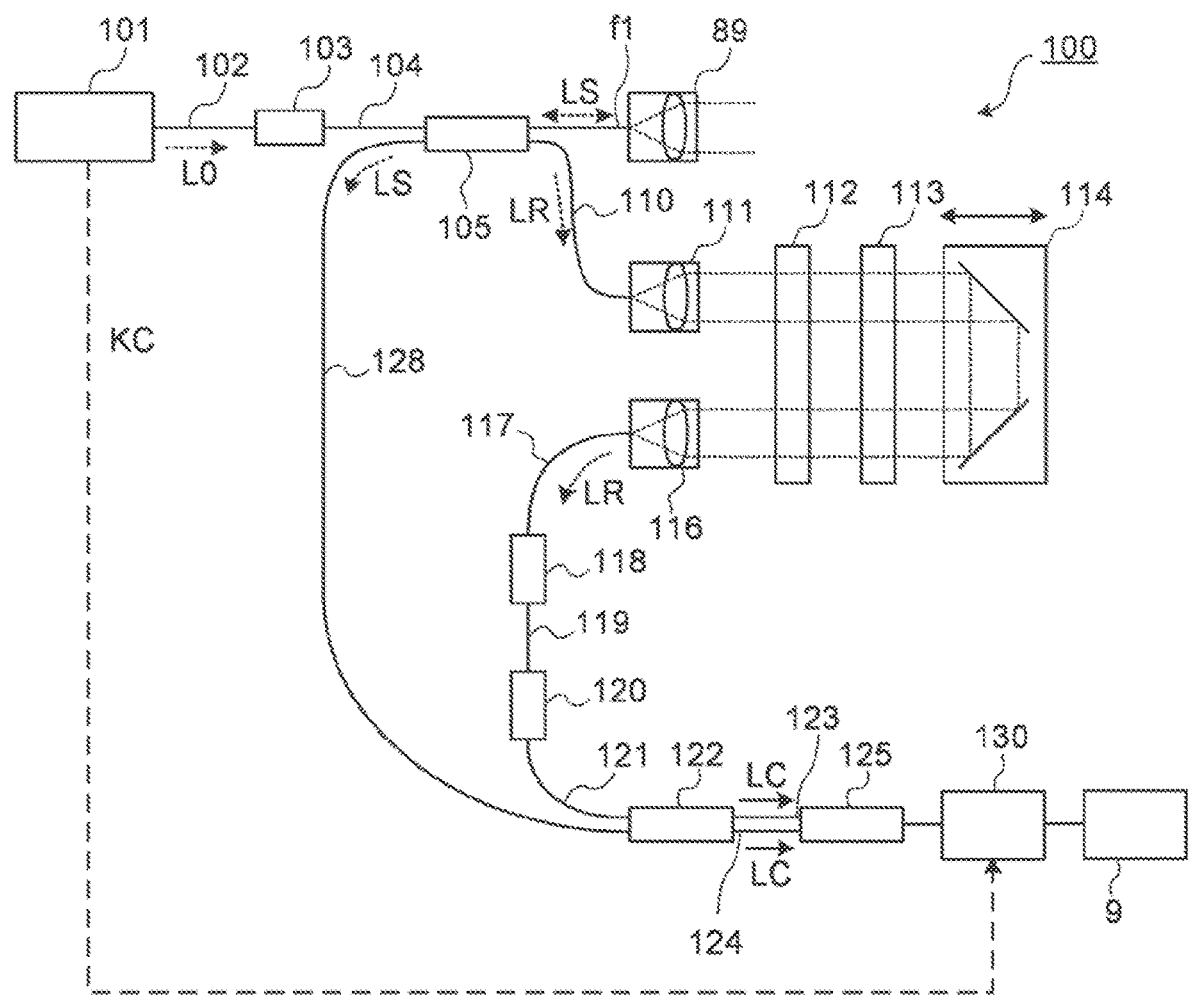
FIG. 2 is a schematic diagram illustrating an example of a configuration of an optical system of the ophthalmologic apparatus according to the embodiments.

The OCT optical system 8 includes an OCT unit 100. As illustrated in FIG. 2, in the OCT unit 100, like general swept-source-type OCT apparatuses, an OCT light source 101 includes a wavelength tunable type (a wavelength scanning type) light source capable of sweeping (scanning) the wavelengths of emitted light. The wavelength tunable type light source includes a laser light source that includes a resonator. The OCT light source 101 temporally changes the output wavelength in the near infrared wavelength band which cannot be visually recognized by the human eye.

As illustrated by an example in FIG. 2, the OCT unit 100 is provided with an optical system for performing swept source OCT. This optical system includes an interference optical system. This interference optical system has a function that splits light from the wavelength tunable type (wavelength scanning type) light source into measurement light and reference light, a function that makes the returning light of the measurement light from the subject's eye E and the reference light having traveled through a reference optical path interfere with each other and generates interference light, and a function that detects the interference light. The detection result (detection signal, interference signal) of the interference light obtained by the interference optical system is a signal indicating a spectrum of the interference light, and is sent to the processing unit 9.

The OCT light source 101 includes a near-infrared tunable laser which changing the wavelength of the emitted light (a wavelength range of 1000 nm to 1100 nm) at high speed, for example. The light L0 output from the OCT light source 101 is guided to the polarization controller 103 through the optical fiber 102, and the polarization state of the light L0 is adjusted. The light L0 whose polarization state has been adjusted is guided to the fiber coupler 105 through the optical fiber 104. The fiber coupler 105 splits the light L0 into the measurement light LS and the reference light LR.

The reference light LR is guided to the collimator 111 through the optical fiber 110. The reference light LR is converted into a parallel light beam by the collimator 111. Then, the reference light LR is guided to the corner cube 114 via the optical path length correction member 112 and the dispersion compensation member 113. The optical path length correction member 112 acts so as to match the optical path length of the reference light LR with the optical path length of the measurement light LS. The dispersion compensation member 113 acts so as to match the dispersion characteristics between the reference light LR and the measurement light LS. The corner cube 114 is movable in the incident direction of the reference light LR. With this, the length of the optical path of the reference light LR is changed.

The reference light LR that has traveled through the corner cube 114 passes through the dispersion compensation member 113 and the optical path length correction member 112, is converted from the parallel light beam to the convergent light beam by a collimator 116, and enters an optical fiber 117. The reference light LR that has entered the optical fiber 117 is guided to a polarization controller 118, and the polarization state of the reference light LR is adjusted. Then the reference light LR is guided to an attenuator 120 through an optical fiber 119, and the light amount of the reference light LR is adjusted. After that, the reference light LR is guided to a fiber coupler 122 through an optical fiber 121.

Meanwhile, the measurement light LS generated by the fiber coupler 105 is guided through the optical fiber f1, is made into the parallel light beam by the collimator lens unit 89, is reflected by the dichroic mirror 83 via an optical scanner 88, the focusing lens 87, relay lens 85, and the reflective mirror 84.

The optical scanner 88 deflects the measurement light LS in a one-dimensionally or two-dimensional manner. The optical scanner 88 includes a first galvano mirror and a second galvano minor, for example. The first galvano mirror deflects the measurement light LS so as to scan the photographing site (fundus Ef or the anterior segment) in a horizontal direction orthogonal to the optical axis of the OCT optical system 8. The second galvano mirror deflects the measurement light LS deflected by the first galvano mirror so as to scan the photographing site in a vertical direction orthogonal to the optical axis of the OCT optical system 8. Examples of scan modes with the measurement light LS performed by the optical scanner 88 like this include horizontal scan, vertical scan, cross scan, radial scan, circle scan, concentric scan, helical (spiral) scan, and the like.

The measurement light LS reflected by the dichroic mirror 83 passes through the relay lens 82, is reflected by the reflective mirror 81, penetrates the dichroic mirror 67, is reflected by the dichroic mirror 52, is refracted by the objective lens 51, and is incident on the subject's eye E. The measurement light LS is scattered and reflected at various depth positions of the subject's eye E. The returning light of the measurement light LS from the subject's eye E advances in the same path as the forward path in the opposite direction, is guided to the fiber coupler 105, and then reaches the fiber coupler 122 via the optical fiber 128.

The fiber coupler 122 combines (interferes) the measurement light LS incident through the optical fiber 128 and the reference light LR incident through the optical fiber 121 to generate interference light. The fiber coupler 122 splits the interference light at a predetermined splitting ratio (e.g., 1:1) to generate a pair of interference light LC. The pair of interference light LC are guided to a detector 125 through optical fibers 123 and 124, respectively.

The detector 125 is a balanced photodiode, for example. The balanced photodiode includes a pair of photodetectors that respectively detect the pair of interference light LC and output the difference between a pair of detection results acquired by the pair of photodetectors. The detector 125 sends the output (detection signal) to the data acquisition system (DAQ) 130.

The DAQ 130 is fed with a clock KC from the OCT light source 101. The clock KC is generated in the OCT light source 101 in synchronization with the output timing of each wavelength within a predetermined wavelength range performed by the wavelength tunable type light source. For example, the OCT light source 101 optically delays one of the two pieces of branched fight obtained by branching the fight L0 of each output wavelength, and then generates the clock KC based on the result of the detection of the combined light of the two pieces of branched light. The DAQ 130 performs sampling the detection signal input from the detector 125 based on the clock KC. The DAQ 130 sends the result of sampling the detection signal from the detector 125 to an arithmetic processor 220. For example, the arithmetic processor 220 performs the Fourier transform, etc. on the spectral distribution based on the sampling data for each series of wavelength scanning (i.e., for each A line). With this, the reflection intensity profile for each A line is formed. In addition, the arithmetic processor 220 forms image data by applying imaging processing to the reflection intensity profiles of the respective A lines.

In the present example, the corner cube 114 is provided for changing the length of the optical path of the reference light LR (reference optical path, reference arm); however, the difference between the measurement optical path length and the reference optical path length may be changed using another kind of optical member.

The processing unit 9 calculates the eye refractive power from the result of the measurement obtained by using the refractometry optical system, and controls the refractometry light source 61 and the focusing lens 74 to move respectively to positions where the fundus Ef, the refractometry light source 61, and the imaging element 59 are conjugate with each other in the optical axis direction based on the calculated eye refractive power. In some embodiments, the processing unit 9 controls the focusing lens 87 of the OCT optical system 8 to move in its optical axis direction in conjunction with the movement of the focusing lens 74. In some embodiments, the processing unit 9 controls the liquid crystal panel 41 (fixation unit 40) to move in the optical axis direction in conjunction with the movement of the refractometry light source 61 and the focusing lens 74.

<Configuration of Processing System>

Figure 4:
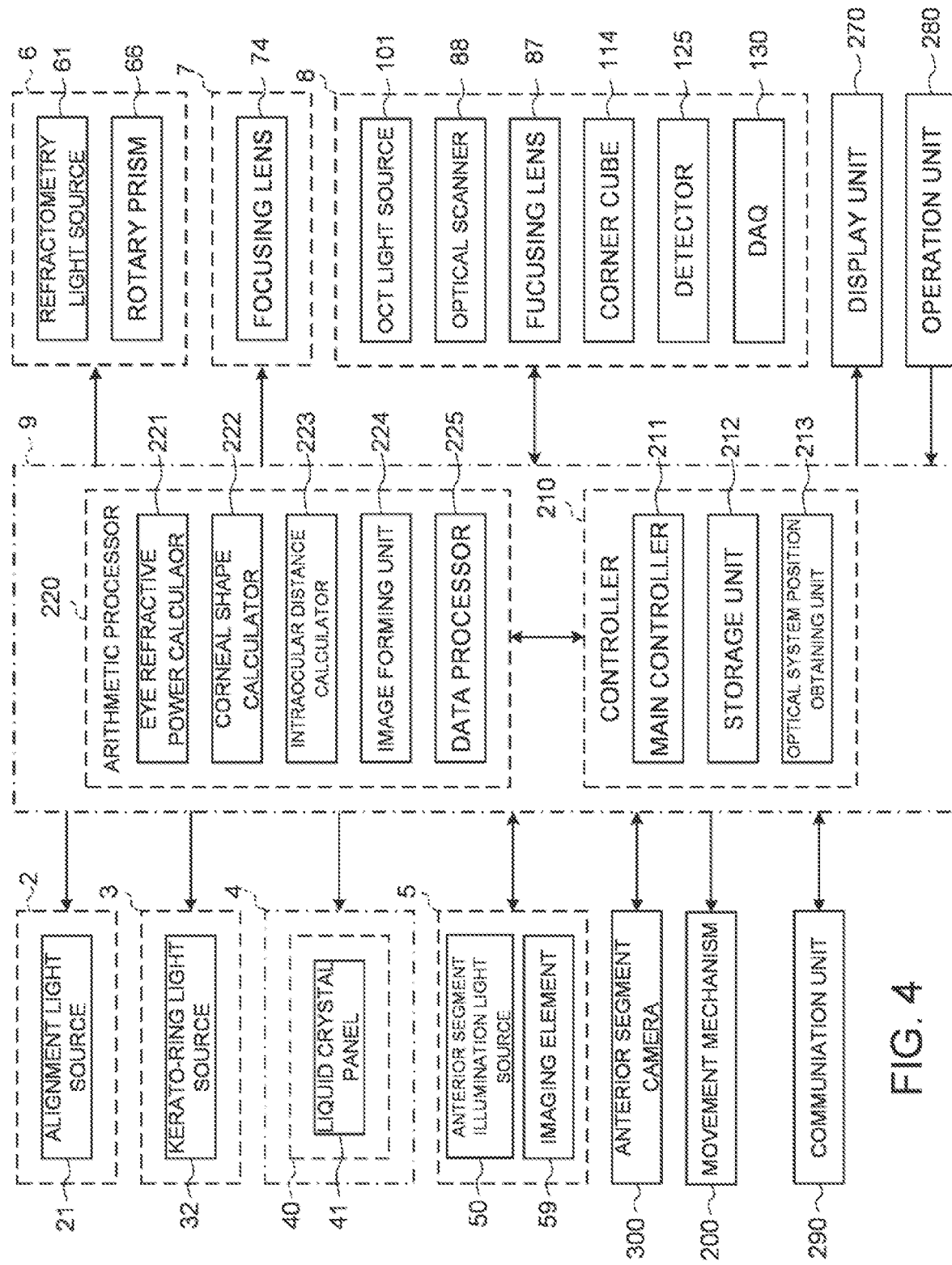
FIG. 4 is a schematic diagram for explaining a processing system of the ophthalmologic apparatus of the embodiments.
Figure 5:
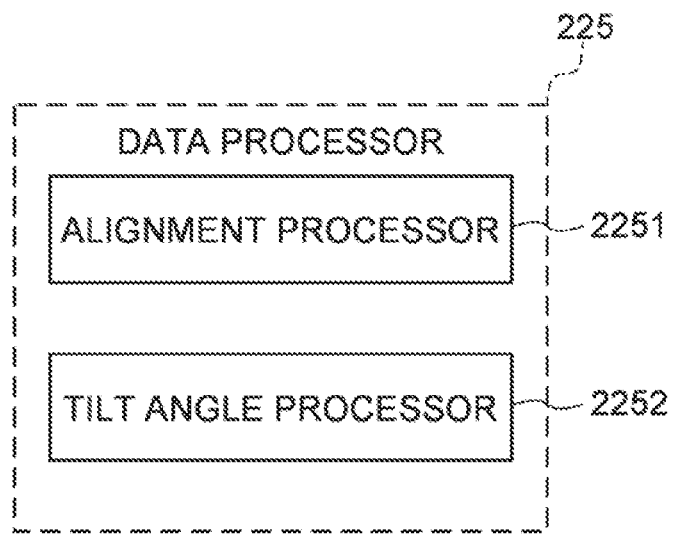
FIG. 5 is a schematic diagram for explaining a processing system of the ophthalmologic apparatus of the embodiments.
Figure 6:
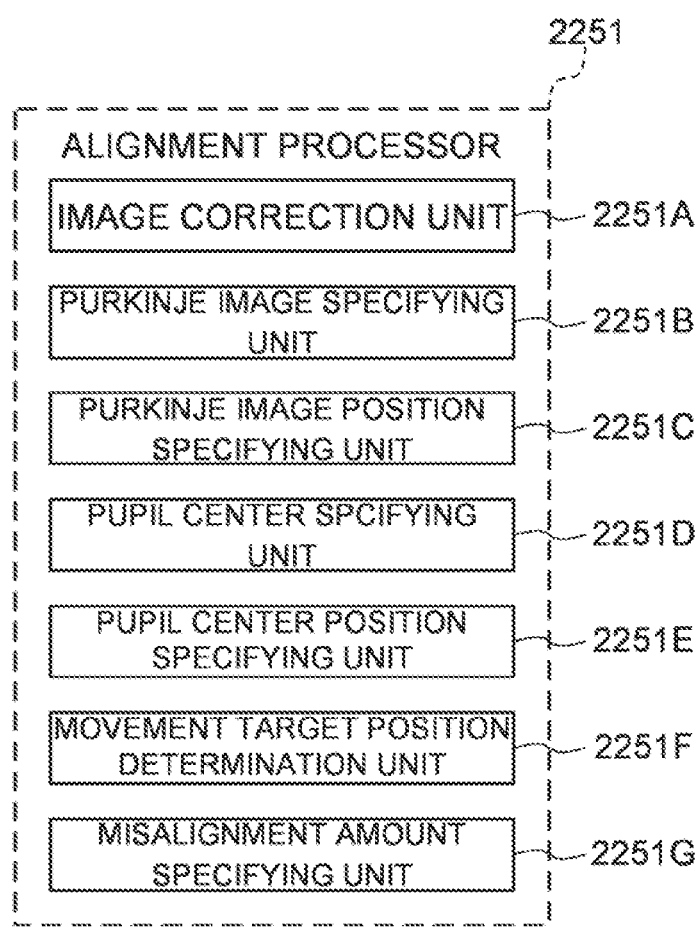
FIG. 6 is a schematic diagram for explaining a processing system of the ophthalmologic apparatus of the embodiments.
Figure 7:
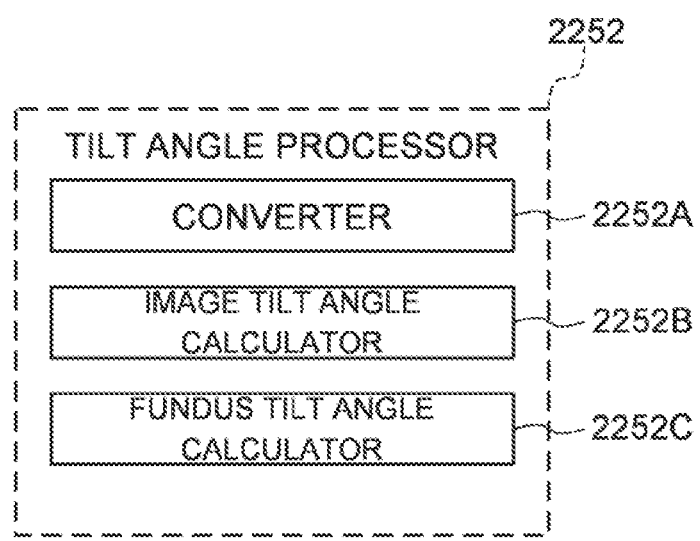
FIG. 7 is a schematic diagram for explaining a processing system of the ophthalmologic apparatus of the embodiments.

The processing system of the ophthalmologic apparatus 1000 will be described. FIGS. 4 to 7 show examples of the functional configuration of the processing system of the ophthalmologic apparatus 1000. FIG. 4 shows an example of a functional block diagram illustrating the processing system of the ophthalmologic apparatus 1000. FIG. 5 shows an example of a functional block diagram of a data processor 225. FIG. 6 shows an example of a functional block diagram of an alignment processor 2251. FIG. 7 shows an example of a functional block diagram of a tilt angle processor 2252.

The processing unit 9 controls each part of the ophthalmologic apparatus 1000. Further, the processing unit 9 is capable of performing various types of arithmetic processing. The processing unit 9 includes a processor. The function of the processor is implemented by a circuit(s) such as, for example, a CPU (central processing unit), a GPU (graphics processing unit), an ASIC (application specific integrated circuit), and a PLD (programmable logic device). Examples of PLD include a simple programmable logic device (SPUD), a complex programmable logic device (CPLD), and a field programmable gate array (FPGA). The processing unit 9 realizes the function according to the embodiments, for example, by read out a computer program stored in a storage circuit or a storage device and executing the computer program.

The processing unit 9 is an example of the "ophthalmologic information processing apparatus" according to the embodiments. That is, the program for realizing the function of the processing unit 9 is an example of the "ophthalmologic information processing program" according to the embodiments.

The processing unit 9 includes a controller 210 and the arithmetic processor 220. Further, the ophthalmologic apparatus 1000 includes the movement mechanism 200, the display unit 270, an operation unit 280, and a communication unit 290.

The movement mechanism 200 is a mechanism for moving the head unit in front, back, left and right directions, the head unit housing the optical systems (optical systems of the apparatus) such as the alignment light projection system 2, the keratometry system 3, the fixation projection system 4, the anterior segment observation system 5, the refractometry projection system 6, the refractometry light reception system 7, the OCT optical system 8, and the like. For example, the movement mechanism 200 is provided with an actuator that generates driving force for moving the head unit and a transmission mechanism that transmits the driving force to the head unit. The actuator is configured by a pulse motor, for example. The transmission mechanism is configured by a combination of gears, a rack and pinion, and the like, for example. The controller 210 (main controller 211) controls the movement mechanism 200 by sending a control signal to the actuator.

The control for the movement mechanism is used for alignment and tracking. Here, tracking is to move the optical system of the apparatus according to the movement of the subject's eye E. To perform tracking, alignment and focus adjustment are performed in advance. The tracking is a function of maintaining a suitable positional relationship in which alignment and focusing are matched by causing the position of the optical system of the apparatus and the like to follow the eye movement.

(Controller 210)

The controller 210 includes a processor and controls each part of the ophthalmologic apparatus 1000. The controller 210 includes the main controller 211 and a storage unit 212. The storage unit 212 stores, in advance, a computer program for controlling the ophthalmologic apparatus 1000. Examples of the computer programs include a program for controlling the light source, a program for controlling the detector, a program for controlling the optical scanner, a program for controlling alignment, a program for controlling tracking, a program for arithmetic processing, a program for user interface, and the like. The main controller 211 operates according to the computer programs, and thereby the controller 210 performs the control processing.

The main controller 211 performs various controls of the ophthalmologic apparatus, as a measurement controller.

Examples of control for the alignment light projection system 2 include control of the alignment light source 21, and the like. Examples of the control of the alignment light source 21 include turning on and off of the light source, adjustment of light amount, adjustment of aperture, and the like. Thereby, the alignment light source 21 can be switched between lighting and non-lighting, or light amount can be changed.

Examples of control for the keratometry system 3 include control of the kerato-ring light source 32, and the like. Examples of the control of the kerato-ring light source 32 include turning on and off of the light source, adjustment of light amount, adjustment of aperture, and the like. Thereby, the kerato-ring light source 32 can be switched between lighting and non-lighting, or light amount can be changed. The main controller 211 controls the arithmetic processor 20 to perform a known calculation on a kerato-ring image detected by the imaging element 59. Thereby, corneal shape parameters of the subject's eye E are obtained.

Examples of control for the fixation projection system 4 include control of the liquid crystal panel 41, movement control of the fixation unit 40, and the like. Examples of the control of the liquid crystal panel 41 include displaying on and off of the visual targets, switching the display position of the fixation target, and the like.

For example, the fixation projection system 4 includes a movement mechanism that moves the liquid crystal panel 41 (or the fixation unit 40) in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move at least the liquid crystal panel 41 in the optical axis direction. Thereby, the position of liquid crystal panel 41 is adjusted so that the liquid crystal panel 41 and the fundus Ef are optically conjugate with each other.

Examples of control for the anterior segment observation system 5 include control of anterior segment illumination light source 50, control of the imaging element 59, and the like. Examples of the control of the anterior segment illumination light source 50 include turning on and off the light sources, adjustment of light amount, adjustment of apertures, and the like. Thereby, the anterior segment illumination light source 50 can be switched between lighting and non-lighting, or light amount can be changed. Example of the control of the imaging element 59 include adjustment of exposure of the imaging element 59, adjustment of gain of the imaging element 59, adjustment of detecting rate of the imaging element 59, and the like. The main controller 211 acquires a signal detected by the imaging element 59 and controls the arithmetic processor 220 to perform processing such as forming image based on the acquired signal and the like.

Examples of the control for the anterior segment cameras 300 include synchronous control of imaging start timings of the two or more anterior segment cameras or imaging timings of respective frames, exposure adjustment of each of the anterior segment cameras, gain adjustment, frame rate adjustment, and the like. Thereby, the anterior segment of the subject's eye E is substantially simultaneously photographed.

Examples of control for the refractometry projection system 6 include control of the refractometry light source 61, control of the rotary prism 66, and the like. Examples of the control of the refractometry light source 61 include turning on and off of the light source, adjustment of light amount, adjustment of aperture, and the like. Thereby, the refractometry light source 61 can be switched between lighting and non-lighting, or light amount can be changed. For example, the refractometry projection system 6 include a movement mechanism that moves the refractometry light source 61 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the refractometry light source 61 in the optical axis direction. Examples of the control of the rotary prism 66 include control of rotating the rotary prism 66 and the like. For example, a rotary mechanism that rotates the rotary prism 66 is provided and the main controller 211 controls the rotary mechanism to rotate the rotary prism 66.

Examples of control for refractometry light reception system 7 include control of the focusing lens 74, and the like. Examples of the control of the focusing lens 74 include control of moving the focusing lens 74 in the optical axis direction. For example, the refractometry light reception system 7 include a movement mechanism that moves the focusing lens 74 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the focusing lens 74 in the optical axis direction. The main controller 211 is capable of moving the refractometry light source 61 and the focusing lens 74 respectively depending on the refractive power of the subject's eye E for example so that the refractometry light source 61 and the fundus Ef and the imaging element 59 are optically conjugate with each other.

Examples of control for the OCT optical system 8 include control of the OCT light source 101, control of the optical scanner 88, control of the focusing lens 87, control of the corner cube 114, control of the detector 125, control of the DAQ 130, and the like. Examples of the control of the OCT light source 101 includes turning on and off of the light source, adjustment of light amount, adjustment of aperture, and the like. Examples of the control of the optical scanner 88 include control of the scanning position and the scanning area and the scanning speed by means of the first galvano mirror, control of the scanning position and the scanning area and the scanning speed by means of the second galvano mirror, and the like.

Examples of the control of the focusing lens 87 include control of moving the focusing lens 87 in the optical axis direction, control of moving the focusing lens 87 to the in-focus reference position corresponding to the photographing site, control of moving the focusing lens 87 within the movement range (in-focus range) corresponding to the photographing site, and the like. For example, the OCT optical system 8 include a movement mechanism that moves the focusing lens 87 in the optical axis direction. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the focusing lens 87 in the optical axis direction. In some embodiments, a holding member that holds the focusing lens 74 and the focusing lens 87, and the driver that drives the holding member are provided in the ophthalmologic apparatus 1000. The main controller 211 controls the driver to move the focusing lenses 74 and 87. For example, the main controller 211 may moves the focusing lens 87 alone based on the intensity of the interference signal, after moving the focusing lens 87 in conjunction with the movement of the focusing lens 74.

Examples of the control of the corner cube 114 include control of moving the corner cube 114 along the optical path of the corner cube 114. For example, the OCT optical system 8 include a movement mechanism that moves the corner cube 114 along the optical path. As is the case with the movement mechanism 200, this movement mechanism is provided with an actuator that generates driving force for moving this movement mechanism and a transmission mechanism that transmits the driving force from the actuator to this movement mechanism. The main controller 211 controls the movement mechanism by sending a control signal to the actuator to move the corner cube 114 along the optical path. Examples of the control of the detector 125 include adjustment of exposure of a detecting element, adjustment of gain of a detecting element, adjustment of detecting rate of a detecting element, control of data transfer of detection signal, and the like. The main controller 211 controls the DAQ 130 to perform sampling of the signal detected by the detector 125 and controls the arithmetic processor 220 (an image forming unit 224) to perform processing such as forming image based on the sampled signal and the like.

The main controller 211 is capable of performing a plurality of preliminary operations prior to OCT measurement. Examples of the preliminary operation include focus adjustment, polarization adjustment, and the like. For example, the focus adjustment is performed on the basis of interference sensitivity of OCT measurement. For example, the focus adjustment can be performed by obtaining the position of the focusing lens 87 so as to maximize the interference intensity and moving the focusing lens 87 to the obtained position. To perform the polarization adjustment, the polarization state of the reference light LR is adjusted for optimizing the interference efficiency between the measurement light LS and the reference In addition, as a display controller, the main controller 211 controls the display unit 270 to display the measurement value of the eye refractive power calculated by an eye refractive power calculator 221, the tomographic image formed by the image forming unit 224, and information corresponding to the processing result of the data processor 225 described after.

Further, the main controller 211 performs writing of data into the storage unit 212, and readout of data from the storage unit 212.

(Storage Unit 212)

The storage unit 212 stores various types of data. Examples of the data stored in the storage unit 212 include a measurement result of the objective measurement, a measurement result of the OCT measurement, image data of a tomographic image, image data of an anterior segment image, subject's eye information, aberration information described after, schematic eye data (standard value data) described after, and the like. The subject's eye information includes information on the subject such as identification information of the left eye/right eye.

The aberration information includes, for each of the anterior segment cameras 300, a parameter quantifying the distortion aberration occurred in a photographic image due to effects of the optical system installed therein. Examples of the parameter related to the distortion aberration that the optical system gives to an image include the principal distance, the position of a principal point (in vertical and horizontal directions), the distortion of a lens radiation direction and tangential direction), and the like. The aberration information is constructed as information table information) that associates the identification information of each of the anterior segment cameras 300 and the correction factor corresponding thereto.

The storage unit 212 further stores various types of programs and data to run the ophthalmologic apparatus.

(Optical System Position Obtaining Unit 213)

The optical system position obtaining unit 213 obtains the current position of the optical system of the apparatus for optically acquiring data of the subject's eye E, the optical system of the apparatus being installed in the ophthalmologic apparatus 1000.

For example, the optical system position obtaining unit 213 receives information representing the content of the movement control of the movement mechanism 200 from the main controller 211 and obtains the current position of the optical system of the apparatus shown in FIG. 1. In this case, the main controller 211 controls the movement mechanism 200 at a predetermined timing (upon start-up of the apparatus, upon inputting patient information, etc.) and moves the optical system of the apparatus to a predetermined initial position. Thereafter, the main controller 211 records the control content each time the movement mechanism 200 is controlled. Thereby, a history of the control contents can be obtained. The optical system position obtaining unit 213 refers to this history and obtains the control contents up to the present time, and determines the current position of the optical system of the apparatus based on the control contents.

In some embodiments, each time controlling the movement mechanism 200, the main controller 211 send the control content thereof to the optical system position obtaining unit 213. The optical system position obtaining unit 213 sequentially obtains the current position of the optical system of the apparatus each time receiving the control content.

In some embodiments, the optical system position obtaining unit 213 includes a position sensor that detects the position of the optical system of the apparatus.

The main controller 211 is capable of controlling the movement mechanism 200 based on the current position obtained by the optical system position obtaining unit 213 and a movement target position determined by the data processor 225 described after. Thereby, the optical system of the apparatus can be moved to the movement target position. For example, the main controller 211 obtains a difference between the current position and the movement target position. This difference value is a vector value having the current position as a start point and the movement target position as an end point, for example. This vector value is a three-dimensional vector value expressed in the XYZ coordinate system, for example.

(Arithmetic Processor 220)

The arithmetic processor 220 include an eye refractive power calculator 221, a corneal shape calculator 222, an intraocular distance calculator 223, the image forming unit 224, and the data processor 225.

(Eye Refractive Power Calculator 221)

The eye refractive power calculator 221 analyzes a ring image (pattern image) acquired by receiving the returning light of the ring-shaped light flux (ring-shaped measurement pattern) projected onto the fundus Ef by the refractometry projection system 6 by the imaging element 59. For example, the eye refractive power calculator 221 obtains a position of the center of gravity of the ring image from the brightness distribution in the image representing the acquired ring image, obtains brightness distributions along a plurality of scanning directions extending radially from the position of the center of gravity, and specifies the ring image from this brightness distributions. Subsequently, the eye refractive power calculator 221 obtains an approximate ellipse of the specified ring image and obtains a spherical power, an astigmatic power, and an astigmatic axis angle (eye refractive power) by assigning a major axis and a minor axis of the approximate ellipse to a known formula. Alternatively, the eye refractive power calculator 221 can obtain the eye refractive power parameter based on deformation and displacement of the ring image with respect to the reference pattern.

(Corneal Shape Calculator 222)

The corneal shape calculator analyzes a kerato-ring image acquired by receiving the returning light of the ring-shaped light flux projected onto the cornea Cr of the subject's eye E by the keratometry system 3 by the imaging element 59.

The corneal shape information includes an arbitrary parameter value representing the shape of the cornea which can be measured using a known ophthalmologic apparatus, for example. Typically, the corneal shape information includes any one of a radius of curvature (curvature), a direction of a steeper meridian, a radius of curvature (power) along the steeper meridian, a direction of a flatter meridian, a radius of curvature (power) along the flatter meridian, an ellipticity, an eccentricity, an oblateness, a topograph including irregular astigmatism, aberration information using a Zernike polynomial, id the like.

For example, the corneal shape calculator 222 calculates the radius of the corneal curvature of the steeper meridian and/or the flatter meridian of the anterior surface of the cornea by analyzing the acquired kerato-ring image and calculates the parameters representing the corneal shape based on the radius of the corneal curvature. The corneal shape calculator 222 can calculate the radius of the corneal curvature by applying arithmetic processing to the acquired kerato-ring image and calculate the corneal refractive power, the corneal astigmatic power, and the corneal astigmatic axis angle from the calculated the radius of the corneal curvature.

(Intraocular Distance Calculator 223)

The intraocular distance calculator 223 obtains one or more intraocular distance in the subject's eye E based on detection results of the interference light LC acquired by the OCT optical system 8. The one or more intraocular distance include(s) an axial length (distance from conical apex to inner limiting membrane). In some embodiments, the intraocular distance calculator 223 specifies a peak position of the detection result (interference signal) of the interference light LC corresponding to a predetermined site in the eye by analyzing the detection result of the interference fight LC acquired by the OCT optical system 8, and obtains the above intraocular distance based on the distance between the specified peak positions. In some embodiments, the intraocular distance calculator 223 further obtains a corneal thickness, an anterior chamber depth, a lens thickness, a length of vitreous cavity, a choroidal thickness, and the like.

(Image Forming Unit 224)

The image forming unit 224 forms image data of a tomographic image of the fundus Ef based on a signal detected by the detector 125. That is, the image forming unit 224 forms the image data of the subject's eye E based on a detection result of the interference light LC obtained by the interference optical system. Like the conventional spectral-domain-type OCT, this process includes processes such as filtering and FFT (Fast Fourier Transform). The image data acquired in this manner is a data set including a group of image data formed by imaging the reflection intensity profiles of a plurality of A lines. Here, the A lines are the paths of the measurement light LS in the subject's eye E.

In order to improve the image quality, it is possible to repeatedly perform scan with the same pattern a plurality of times to collect a plurality of data sets, and to compose (i.e., average) the plurality of data sets.

(Data Processor 225)

The data processor 225 performs various kinds of data processing (e.g., image processing) and various kinds of analysis on a tomographic image formed by the image forming unit 224. For example, the data processor 225 performs various correction processes such as brightness correction and dispersion correction of images. Further, the data processor 225 performs various types of image processing and analysis on images (anterior segment image, etc.) acquired using the observation system 5.

The data processor 225 can form volume data (voxel data) of the subject's eye E by performing known image processing such as interpolation processing for interpolating pixels between tomographic images. In the case of displaying an image based on the volume data, the data processor 225 performs a rendering processing on the volume data so as to form a pseudo three-dimensional image viewed from a specific line-of-sight direction.

As shown in FIG. 5, the data processor 225 includes the alignment processor 2251 and the tilt angle processor 2252. The alignment processor 2251 performs data processing for performing alignment with reference to the cornea based on the two or more photographic images obtained by the anterior segment cameras 300. The tilt angle processor 2252 performs processing for obtaining a tilt angle of the fundus Ef.

(Alignment Processor 2251)

As shown in FIG. 6, the alignment processor 2251 includes an image correction unit 2251A, a Purkinje image specifying unit 2251B, a Purkinje image position specifying unit 22510, a pupil center specifying unit 2251D, a pupil center position specifying unit 2251E, a movement target position determination unit 2251F, and a misalignment amount specifying unit 2251G.

(Image Correction Unit 2251A)

The image correction unit 2251A corrects distortion of photographic images captured by the anterior segment cameras 300. The image correction unit 2251A can correct the distortion of the photographic images based on the aberration information stored in the storage unit 212. This processing is performed by, for example, known image processing technology based on a correction factor for correcting distortion aberration. Note that, if the distortion aberration caused in photographic images due to the optical system of the anterior segment cameras 300 is sufficiently small or the like, the aberration information and the image correction unit 2251A are not necessary, (Purkinje Image Specifying Unit 2251B)

The main controller 211 turns of the alignment light source 21, for example. Thereby, alignment light flux is projected onto the anterior segment and a Purkinje image is formed. The Purkinje image is formed in a position displaced from the corneal apex by half of the radius of the corneal curvature in the axis direction (Z direction).

The anterior segment onto which the alignment light flux is projected is substantially simultaneously photographed by the two anterior segment cameras 300. The two photographic images obtained substantially simultaneously by the two anterior segment cameras 300 are corrected by the image correction unit 2251A as necessary and input to the Purkinje image specifying unit 2251B.

The Purkinje image specifying unit 2251B specifies the Purkinje image (image region corresponding to the Purkinje image) by analyzing each of the two photographic images. This specifying processing includes, for example as in the conventional case, a threshold processing related to a pixel value for searching for a bright spot (pixel having high brightness) corresponding to the Purkinje image. Thereby, the image regions in the photographic images corresponding to the Purkinje image are specified.

The Purkinje image specifying unit 2251B can obtain a position of a representative point in the image region corresponding to the Purkinje image. The representative point may be a center point or a center of gravity point of the image region, for example. In this case, the Purkinje image specifying unit 2251B can obtain an approximate circle or an approximate ellipse of the periphery of the image region and can obtain the center point or the center of gravity point of the approximate circle or the approximate ellipse.

(Purkinje Image Position Specifying Unit 2251C)

The Purkinje image position specifying Unit 22510 specifies a position of the Purkinje image specified by the Purkinje image specifying Unit 2251B based on information input from the Purkinje image specifying unit 22513. The position of the Purkinje image may include at least a position in the X direction (X coordinate value) and a position in the Y direction (Y coordinate value), and may further include a position in the Z direction (Z coordinate value).

FIG. 8 schematically shows the two photo a c images acquired by the anterior segment cameras 300.

A photographic image 400A is the photographic image (anterior segment image) acquired by the anterior segment camera 300A. A photographic image 400B is the photographic image acquired by the anterior segment camera 300B. The photographic images 400A and 400B may be images corrected by the image correction unit 2251A.

The photographic image 400A is an image obtained by photographing the anterior segment from a diagonal direction. In the photographic image 400A, a pupil region 401A and a Purkinje image 402A are depicted. The Purkinje image specifying Unit 22518 specifies the Purkinje image 402A in the photographic image 400A.

In the same manner, the photographic image 400B is an image obtained by photographing the anterior segment from a diagonal direction different from the photographic image 400A. In the photographic image 400B, a pupil region 401B and a Purkinje image 402B are depicted. The Purkinje image specifying Unit 2251B specifies the Purkinje image 402B in the photographic image 400B.

The photographic images 400A and 400B are images obtained by photographing from directions different from the optical axis of the objective lens 51. Further, when XY alignment is substantially matched, as shown in FIG. 8, the Purkinje images 402A and 40213 are formed on the optical axis of the objective lens 51.

Visual angles (angles with respect to the optical axis of the objective lens 51) of the anterior segment cameras 300A and 300B are known and the photographing magnification is also known. Thereby, the relative position (three-dimensional position in actual space) of the Purkinje image formed in the anterior segment with respect to the ophthalmologic apparatus 1000 (anterior segment cameras 300A and 300B) can be obtained based on the position of the Purkinje image 402A in the photographic image 400A and the position of the Purkinje image 402B in the photographic images 400B.

Further, the relative position between the pupil of the subject's eye E and the Purkinje image formed in the anterior segment can be obtained based on the relative position (misalignment amount) between the pupil region 401A and the Purkinje image 402A in the photographic image 400A and the relative position (misalignment amount) between the pupil region 401B and the Purkinje image 402B in the photographic image 400B.

(Pupil Center Specifying Unit 2251D)

The pupil center specifying unit 2251D specifies a position in the photographic image corresponding to a predetermined characteristic point of the anterior segment by analyzing each photographic image obtained by the anterior segment cameras 300 or the image corrected for distortion aberration by image correction unit 2251A. In the present embodiment, the pupil center of the subject's eye E is specified. It should be noted that the center of gravity of the pupil may be obtained as the pupil center. It is also possible to configure such that the characteristic point other than the pupil center (the center of gravity of the pupil) is specified.

The pupil center specifying unit 2251D specifies the image region (pupil region) corresponding to the pupil of the subject's eye E based on the distribution of pixel values (luminance values etc.) in the photographic image. Generally, the pupil is represented with lower luminance compared to other parts, and therefore, the pupil region may be specified by searching an image region with low luminance. At this time, the pupil region may be specified by taking the shape of the pupil into consideration. That is, it is possible to configure such that the pupil region is specified by searching for a substantially circular image region with low luminance.

Next, the pupil center specifying unit 2251D specifies the center position of the specified pupil region. As mentioned above, the pupil is substantially circular. Accordingly, by specifying the contour of the pupil region and then specifying the center position of an ellipse approximating this contour, this may be used as the pupil center. Instead, by obtaining the center of gravity of the pupil region, this center of gravity may be used as the pupil center.

Note that, even when other characteristic points are employed, the position of the characteristic point can be specified based on the distribution of pixel values in the photographic image in the same manner as mentioned above.

(Pupil Center Position Specifying Unit 2251E)

The pupil center position specifying unit 2.2.51E specifies the three-dimensional position of the pupil center of the subject's E, based on the positions of the two anterior segment cameras 300 (and the photographing magnification) and the positions of the pupil center in the two photographic images specified by the pupil center specifying unit 225ID.

Figure 9A:
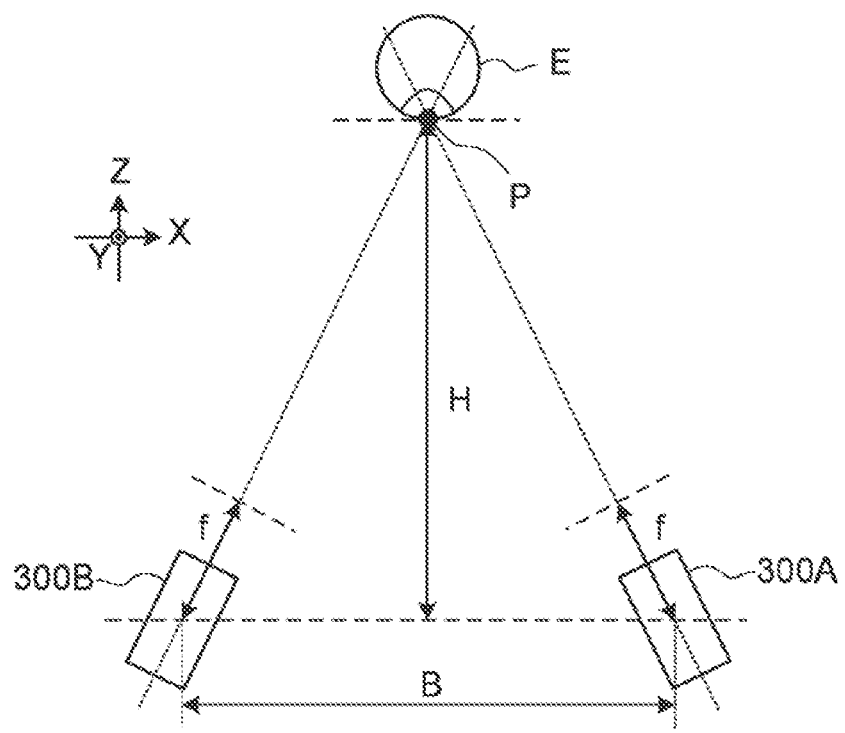
FIG. 9A is a schematic diagram for explaining an operation of the ophthalmologic apparatus of the embodiments.
Figure 9B:
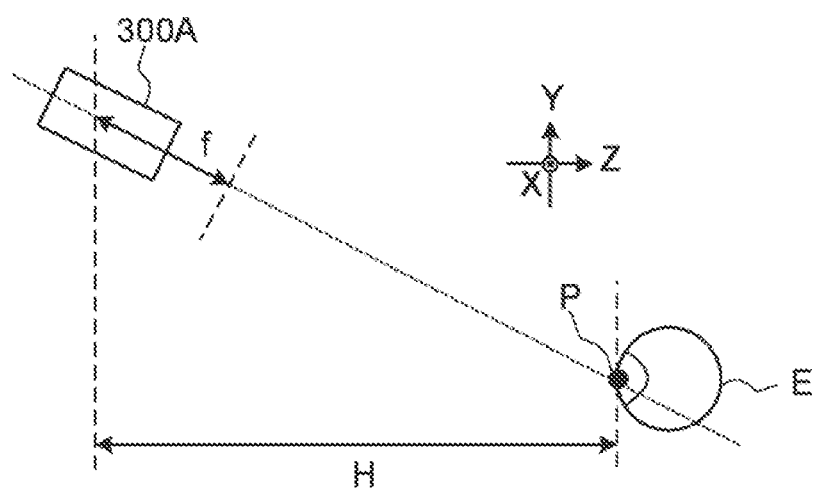
FIG. 9B is a schematic diagram for explaining an operation of the ophthalmologic apparatus of the embodiments.

FIG. 9A is a top view illustrating the positional relationship between the subject's eye E and anterior segment cameras 300A and 300B. FIG. 9B is a side view illustrating the positional relationship between the eye E and the anterior segment cameras 300A and 300B. The distance (base line length) between the two anterior segment cameras 300A and 300B is represented as "B". The distance (photographing distance) between the base line of the two anterior eye cameras 300A and 300B and a characteristic site P of the eye E is represented as "H". Reference letter "f" represents the distance (screen distance) between each of the anterior segment cameras 300A and 300B and the screen plane.

In this arrangement, the resolution of photographic images obtained by the anterior segment cameras 300A and 300B is expressed by the following equations. In the following equations, $\Delta p$ represents the pixel resolution.

$xy$ resolution (planar resolution): $\Delta xy = H \times \Delta p / f$ $z$ resolution (depth resolution): $\Delta z = H \times \Delta p / (B \times f)$ The pupil center position specifying unit 2251E applies known trigonometry, taking into account the positional relationship illustrated in FIGS. 9A and 8B, to the positions of the two anterior segment cameras 300A and 300B (these are known) and positions corresponding to the pupil center P in the two photographic images, thereby calculating the three-dimensional position of the pupil center P.

(Movement Target Position Determination Unit 2251F)

The movement target position determination unit 2251E determines the movement target position of the optical system of the apparatus based on the position of the Purkinje image specified by the Purkinje image position specifying unit 2251C and the position of the pupil center specified by the pupil center position specifying unit 2251E. For Example, the movement target position determination unit 2251E obtains the difference between the position of the specified Purkinje image and the position of the specified pupil center, and determines the movement target position so that the obtained difference satisfies a predetermined alignment completion condition.

The main controller 211 controls the movement mechanism 200 based on the movement target position determined by the movement target position determination unit 2251F.

(Misalignment Amount Specifying Unit 2251G)

The misalignment amount specifying unit 2251G specifies a misalignment amount between the measurement optical axis of the OCT optical system 8 that alignment has been performed and the eyeball optical axis of the subject's eye E. The measurement optical axis is an optical axis (or the optical axis of the objective lens 51) of the optical system that projects the measurement light LS onto the subject's eye E. The eyeball optical axis may be an arbitrary axis passing through the eyeball such as a visual axis, an ocular axis, and the like. In the case that the OCT measurement is performed while projecting the fixation light flux onto the subject's eye E, the eyeball optical axis is a visual axis. In the present embodiment, the misalignment amount specifying unit 2251G specifies the misalignment amount between the measurement optical axis and the visual axis of the subject's eye E.

The misalignment amount includes a shift amount and a tilt amount between the measurement optical axis and the eyeball optical axis (visual axis). The shift amount corresponds to the deviation amount of the eyeball optical axis in a direction orthogonal to (intersecting) the measurement optical axis. The tilt amount corresponds to an angle between the measurement optical axis and the eyeball optical axis.

The misalignment amount specifying unit 2251G is capable of specifying the shift amount (unit: millimeter) based on a misalignment amount between the position of the Purkinje image specified by the Purkinje image position specifying unit 2251C and a predetermined reference position. Examples of the predetermined reference position includes a position of the measurement optical axis, and the like. The misalignment amount specifying unit 2251G specifies, for example, the difference of the position of the Purkinje image with respect to the position of the measurement optical axis at the position in the Z direction of the Purkinje image, as the shift amount (unit: millimeter).

The misalignment amount specifying unit 2251E is capable of specifying the tilt amount (unit: degree) based on a misalignment amount between the position of the Purkinje image specified by the Purkinje image position specifying unit 2251C and the position of the pupil center specified by the pupil center position specifying unit 2251E. The misalignment amount specifying unit 2251G specifies, for example, a direction of the eyeball optical axis (visual axis) from the position of the Purkinje image and the position of the pupil center, and specifies an angle between the specified direction of the visual axis and the measurement optical axis, as the tilt amount.

The misalignment amount specifying unit 2251G is capable of specifying the misalignment amount during at least the OCT measurement. In some embodiments, the position of the Purkinje image and the position of the pupil center are sequentially specified based on the photographic images obtained sequentially by the anterior segment cameras 300. And the misalignment amount specifying unit 2251G specifies the misalignment amount in real time.

(Tilt Angle Processor 2252)

As shown in FIG. 7, the tilt angle processor 2252 includes a converter 2252A, an image tilt angle calculator 2252B, and a fundus tilt angle calculator 2252C.

(Converter 2252A)

The converter 2252A converts a distance designated in the tomographic image formed by the image forming unit 224 into a value corresponding to the actual dimension. The converter 2252A converts the distance in the Z direction in the tomographic image with reference to the pixel spacing value Δp (unit: micrometer/pixel) in the eyeball tissue, the pixel spacing value being unique to the optical system of the apparatus. The converter 2252A converts the distance in the XY directions (OCT measurement rage) in the tomographic image with reference to size information generated as follows.

For example, the converter 2252A generates the size information using the schematic eye data, which is standard value data, and the measurement value of the optical characteristic of the subject's eye E. Examples of the schematic eye data include Gullstrand's schematic eye data, Helmholtz's schematic eye data, and the like. Examples of the measurement value of the optical characteristic include at least one of the radius of the corneal curvature, the eye refractive power, and the axial length. The radius of the corneal curvature can he obtained using the keratometry system 3. The eye refractive power can be obtained using the refractometry projection system 6 and the refractometry light reception system 7. The axial length can be obtained using the OCT optical system 8. Such the processing by the converter 2252A may be similar to the processing disclosed in Japanese Unexamined Patent Application Publication No. 2016-043155.

The converter 2252A generates the size information using the schematic eye data and the measurement value acquired by the ophthalmologic apparatus 1000. In this generation processing of the size information, for a parameter which can be measured by using the ophthalmologic apparatus 1000 among parameters included in the schematic eye data, the measurement value acquired by the ophthalmologic apparatus 1000 is used.

In the present embodiment, the converter 2252A is capable of generating the size information by performing magnification correction based on the acquired measurement value. For example, the converter 2252A obtains the magnification by the eyeball optical system of the subject's eye E, and generates the size information indicating the size for one pixel in the tomographic image of the subject's eve E from the obtained magnification.

As a specific example, first, the converter 2252A calculates the magnification by the eyeball optical system of the subject's eye based on the measurement value of the optical characteristic of the subject's eye E. In the present embodiment, both the magnification by the subject's eye E and the magnification by the OCT optical system 8 are considered in obtaining the photographing magnification. Here, it is assumed that the OCT optical system 8 has a general configuration in which the objective lens 51, the imaging diaphragm (not shown), the variable magnification lens (focusing lens 87), and the relay lens 85 are arranged on the optical axis in order from the subject's eye E side.

First, in a case that the eye refractive power is a measurement value at the corneal apex (corneal refractive power), the converter 2252A converts it to the refractive power at the pupil (pupil refractive power) as necessary. This calculation can be executed based on, for example, a spectacle wearing distance and a distance from the corneal apex to the entrance pupil as conventional.

Next, the converter 2252A calculates the imaging position by the objective lens 51. This calculation can be executed by the Newton equation based on, for example, the pupil refractive power, the focal length of the objective lens 51, and a distance from the entrance pupil to the front focal point of the objective lens 51.

Next, the converter 2252A calculates the photographing magnification by the variable magnification lens (focusing lens). This calculation can be executed by, for example, solving a quadratic equation representing a relation of the calculation result of the imaging position by the objective lens 51 and the focal distance, principal focal length and object to image distance of the variable magnification lens, for the photographing magnification.

Next, the converter 2252A calculates an exit angle from the objective lens 51. This calculation can be executed based on, for example, the result of calculation of the photographing magnification, a distance from the rear principal point of the objective lens 51 to the imaging diaphragm, and the focal length of the objective lens 51. In this case, the exit angle is calculated so that the height of an image on the detection surface of the image becomes a predetermined value. This predetermined value is set to, for example, −0.1 mm (the minus sign indicates that the image is formed in the downward direction from the optical axis).

Next, the converter 2252A calculates an incident angle to the objective lens 51 such that the height of an image on the diaphragm surface of the imaging diaphragm becomes the abovementioned predetermined value. This calculation can be executed based on, for example, the result of calculation of the exit angle from the objective lens 51 and the angular magnification of the entrance pupil and the imaging diaphragm.

Next, the converter 2252A calculates the radius of curvature of the rear surface of the cornea of the subject's eye E. This calculation can be executed based on, for example, the measurement value of the corneal curvature (curvature of the front surface of the cornea) measured by using the keratometry system 3, and the ratio between the curvatures of the front surface and the rear surface of the cornea. As the ratio of the curvature, it is possible to use, for example, a value of the schematic eye data. In the case of measuring the curvature (radius of curvature) of the rear surface of the cornea Cr by using the OCT optical system 8, it is possible to use the measurement value as the radius of curvature of the rear surface of the cornea.

Next, the converter 2252A calculates the distance between a far point and an object (corneal apex). This calculation can be executed based on, for example, the refractive power at the corneal apex, and the spectacle wearing distance.

Next, the converter 2252A calculates the distance from the rear surface of the lens of the subject's eye E to the retinal surface (fundus Ef). This calculation can be executed, for example, by paraxial ray tracing based on the measurement value and calculated value of the curvature (radius of curvature) of the cornea Cr. In this case, as an eyeball optical constant, for example, a value of the schematic eye data can be used.

Next, the optical constant of the eyeball optical system of the subject's eye E is determined. Then, as the optical constant of the subject's eye E, for example, the measurement value and calculation result of the curvature (radius of curvature) of the cornea, and the measurement values of the refractive power and axial length are used. Further, as the radius of curvature of the retinal surface (fundus), a half value of the measurement value of the axial length is used. Further, as the distance from the rear surface of the lens to the retina (fundus), a value obtained by subtracting the measurement value obtained by using the OCT optical system 8 or a standard value (value of the schematic eye data) of the distance from the corneal front surface to the rear surface of the lens from the measurement value of the axial length is used.

When the optical constant of the subject's eye E is determined, the converter 2252A calculates the height of an image on the retinal surface (fundus). This calculation can be executed by, for example, ray tracing using the determined optical constant and the result of calculation of the incident angle to the objective lens 51.

Finally, the converter 2252A calculates the magnification based on the calculation result of the height of the image on the retinal surface, the calculation result of the height of the image on the detection surface, the relay magnification of a relay lens (the influence of the imaging optical system and so on), and the like. This magnification is obtained considering the magnification of the eyeball optical system of the subject's eye E and the magnification of the imaging optical system.

The converter 2252A obtains the length (unit: micrometer/pixel) of each pixel in vertical and horizontal directions in the tomographic image from the obtained magnification, as the size information. For example, the converter 2252A includes table information in which the lengths in the vertical and horizontal directions for one pixel are associated with each of a plurality of magnifications in advance, and obtains the lengths for one pixel in vertical and horizontal directions in the tomographic image from the obtained magnification by referring to the table information. Instead of the table information on a plurality of discrete magnification values, graph information, in which a continuous change in the magnification values is associated with a change in the size for one pixel, can also be used.

(Image Tilt Angle Calculator 2252B)

The image tilt angle calculator 2252B calculates a tilt angle of the fundus Ef in the tomographic image of the subject's eye E formed by the image forming unit 224. The image tilt angle calculator 2252B obtains, for example, a predetermined layer region specified by the known segmentation processing performed by the data processor 225. Examples of the predetermined layer region include the inner limiting membrane, the nerve fiber layer, the ganglion cell layer, the inner plexiform layer, the inner nuclear layer, the outer plexiform layer, the outer nuclear layer, the external limiting membrane, the photoreceptor layer, the retinal pigment epithelium layer, and the like.

Figure 10:
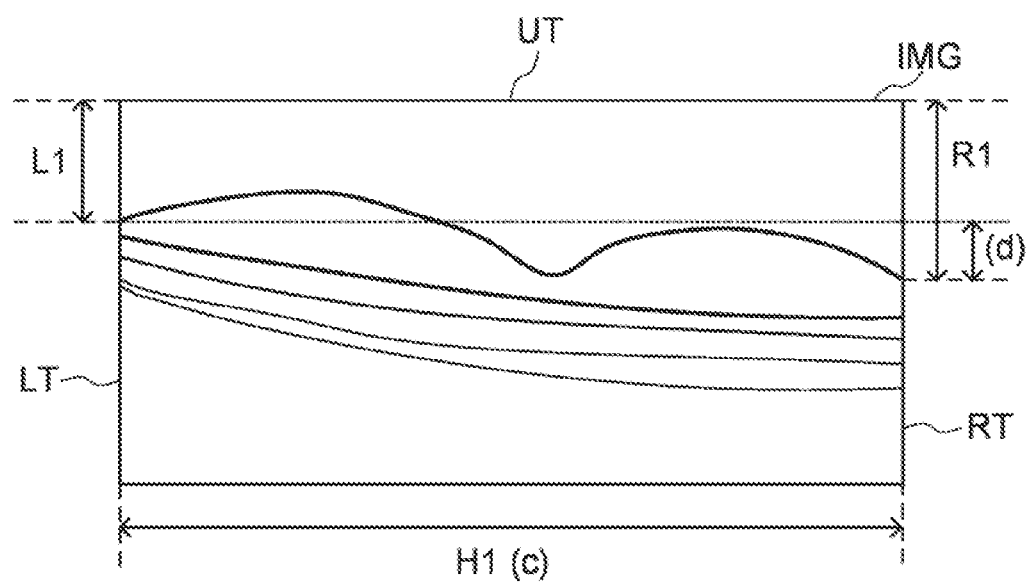
FIG. 10 is a schematic diagram for explaining an operation of the ophthalmologic apparatus of the embodiments.

FIG. 10 schematically shows the tomographic image of the fundus Ef according to the embodiments.

In FIG. 10, at the left end LT of the frame of the tomographic image IMG, the distance in the vertical direction from the upper end UT of the frame to the image region of the site corresponding to the predetermined layer region (for example, the nerve fiber layer) in the fundus Ef is set as L1. In the same manner, at the right end RT of the frame of the tomographic image IMG, the distance in the vertical direction from the upper end UT of the frame to the image region of the site is set as R1. The converter 2252A multiplies the difference (|R1−L1|) in the vertical direction of the image region of the site between at the left end LT of the frame of the tomographic image IMG and at the right end RT of the frame by the pixel spacing value Δp, and thereby obtains a value |d| corresponding to the actual dimension for the difference (|R1−L1|).

Next, the converter 2252A converts the distance H1 in the horizontal direction of the frame of the tomographic image IMG, which is corresponding to the OCT measurement range, into a value c corresponding to the actual dimension using the above size information.

The image tilt angle calculator 2252B obtains the tilt angle g0 (unit: degree) of the tomographic image according to the expression (1).

$$g0 = \arctan(|d|/c) \quad (1)$$

(Fundus Tilt Angle Calculator 252C)

The fundus tilt angle calculator 2252C is capable of calculating the fundus tilt angle by correcting the tilt angle of the tomographic image obtained by the image tilt angle calculator 2252B according to the misalignment amount specified by the misalignment amount specifying unit 2251G.

Specifically, the tilt angle processor 2252 (or the data processor 225) determines the result of specifying the misalignment amount by the misalignment amount specifying unit 2251G. The fundus tilt angle calculator 2252C calculates the fundus tilt angle based on the result of the determination by the tilt angle processor 2252.

<In the Case that the Measurement Optical Axis and the Eyeball Optical Axis Substantially Coincide with Each Other>

Figure 11:
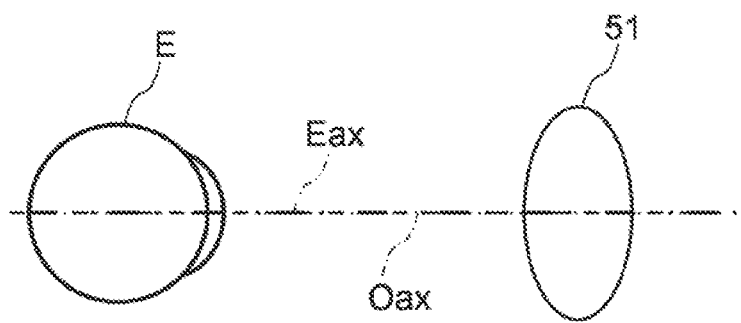
FIG. 11 is a schematic diagram for explaining an operation of the ophthalmologic apparatus of the embodiments.

As shown in FIG. 11, when it is determined by the tilt angle processor 2252 that the measurement optical axis (optical axis of the objective lens 51) Oax and the eyeball optical axis (visual axis) Eax substantially coincide with each other, the fundus tilt angle processor 252C outputs, as the fundus tilt angle g1, the tilt angle g0 of the tomographic without correcting the tilt angle g0. That is, the fundus tilt angle calculator 2252C outputs, as the fundus tilt angle g1, the tilt angle g0 of the tomographic image obtained by the image tilt angle calculator 2252B.

$$g1=g0=\arctan(|d|/c) \quad (2)$$

<In the Case that the Eyeball Optical Axis is Shifted with Respect to the Measurement Optical Axis>

Figure 12:
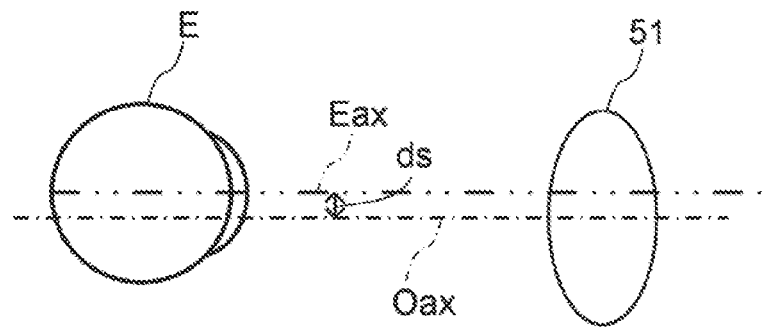
FIG. 12 is a schematic diagram for explaining an operation of the ophthalmologic apparatus of the embodiments.

As shown in FIG. 12, when it is determined 1w the tilt angle processor 2252 that the eyeball optical axis Fax is shifted with respect to the measurement optical axis Oax, the fundus tilt angle processor 2252C obtains the tilt angle g1 by correcting the tilt angle g0 of the tomographic image based on the shift amount ds specified by the misalignment amount specifying unit 2251G.

The fundus tilt angle calculator 2252C obtains the correction angle φ1 according to a linear expression with the shift amount ds as variable shown in expression (3), and then obtains the fundus tilt angle g1 by correcting the tilt angle g0 of the tomographic image using the obtained correction angle φ1 as shown in expression (4). In expression (3), α1 and c1 are constants. For example, α1 and c1 can be obtained by using the schematic eye data.

$$\varphi1=\alpha1 \times ds+c1 \quad (3)$$

$$g1=g0-\varphi1 \quad (4)$$

<In the Case that the Eyeball Optical Axis is Tilted with Respect to the Measurement Optical Axis>

Figure 13:
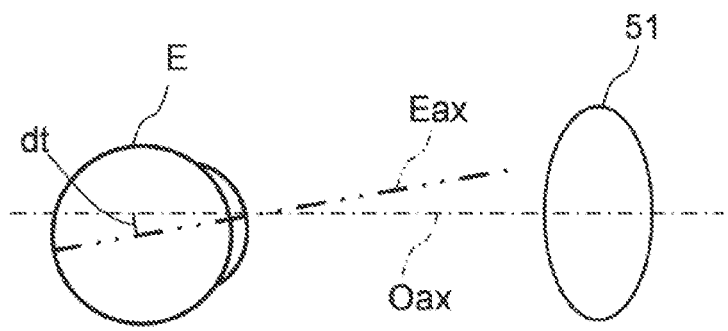
FIG. 13 is a schematic diagram for explaining an operation of the ophthalmologic apparatus of the embodiments.

As shown in FIG. 13, when it is determined by the tilt angle processor 2252 that the eyeball optical axis Eax is tilted with respect to the measurement optical axis Oax, the fundus tilt angle processor 2252C obtains the tilt angle g1 by correcting the tilt angle g0 of the tomographic image based on the tilt amount dt specified by the misalignment amount specifying unit 2251G.

The fundus tilt angle calculator 2252C obtains the correction angle φ2 according to a linear expression with the tilt amount dt as variable shown in expression (5), and then obtains the fundus tilt angle g1 by correcting the tilt angle g0 of the tomographic image using the obtained correction angle φ2 as shown in expression (6). In expression (5), α2 and c2 are constants. For example, α2 and c2 can be obtained by using the schematic eye data.

$$\varphi2=\alpha2 \times dt+c2 \quad (5)$$

$$g1=g0-\varphi2 \quad (6)$$

<In the Case that the Eyeball Optical Axis is Shifted and Tilted with Respect to the Measurement Optical Axis>

Figure 14:
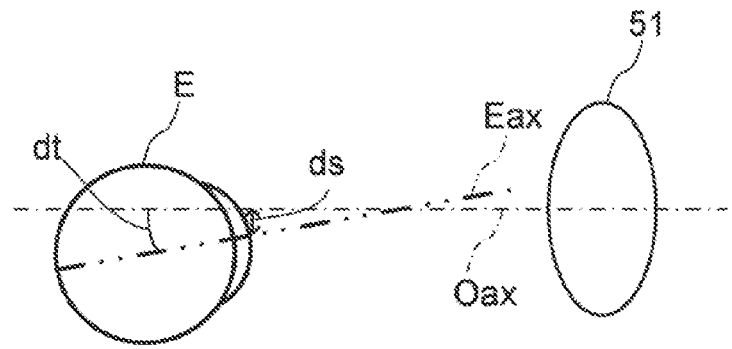
FIG. 14 is a schematic diagram for explaining an operation of the ophthalmologic apparatus of the embodiments.

As shown in FIG. 14, when it is determined by the tilt angle processor 2252 that the eyeball optical axis Fax is shifted and tilted with respect to the measurement optical axis Oax, the fundus tilt angle processor 2252C obtains the tilt angle g1 by correcting the tilt angle g0 of the tomographic image based on the shift amount ds and the tilt amount dt specified by the misalignment amount specifying unit 2251G.

In a range where the shift amount ds and the tilt amount dt are small, the fundus tilt angle calculator 2252C obtains the correction angle φ3 according to an expression with the shift amount ds and the tilt amount dt as variables shown in expression (7), and then obtains the fundus tilt angle g1 by correcting the tilt angle g0 of the tomographic image using the obtained correction angle φ3 as shown in expression (8). In some embodiments, expression (8) is a combining expression obtained by linearly combined an expression for obtaining the correction angle of the shift amount and an expression for obtaining the correction angle of the tilt amount. In expression (7), α3, α4 and c3 are constants. For example, α3, α4, and c3 can be obtained by using the schematic eye data.

$$\varphi3=\alpha3 \times ds \times \alpha4 \times dt+c3 \quad (7)$$

$$g1=g0-\varphi3 \quad (8)$$

The data processor 225 having a configuration as above includes, for example, a processor, a RAM, a ROM, a hard disk drive, a circuit board, and the like. In a storage device such as the hard disk drive, a computer program for causing the processor to execute the processing described above is stored in advance.

(Display Unit 270, Operation Unit 280)

Upon receiving control of the controller 210, the display unit 270 displays information, as a user interface unit. The display unit 270 includes the display unit 10 as illustrated in FIG. 1 and the like.

The operation unit 280 is used to operate the ophthalmologic apparatus, as the user interface unit. The operation unit 280 includes various types of hardware keys (the joystick, buttons, switches, etc.) provided in the ophthalmologic apparatus. Further, the operation unit 280 may include various kinds of software keys (buttons, icons, menus, etc.) displayed on the touch panel type display screen 10a.

At least part of the display unit 270 and of the operation unit 280 may be integrally configured. A typical example of this is the touch-panel display screen 10a.

(Communication Unit 290)

The communication unit 290 has the function of communicating with an external device (not shown). The communication unit 290 has a structure corresponding to the mode of communication with an external device. Examples of the external device includes an eyeglass lens measurement device for measuring the optical properties of lenses. The eyeglass lens measurement device measures the power of the eyeglass lens worn by the subject and inputs the measurement data to the ophthalmologic apparatus 1000. The external device may also be a device (reader) having the function of reading information from a recording medium or a device (writer) having the function of writing information to a recording medium. Further, the external device may be a hospital information system (HIS) server, a Digital Imaging and Communications in Medicine (DICOM) server, a doctor terminal, a mobile terminal, a personal terminal, a cloud server, or the like. The communication unit 290 may be provided in the processing unit 9, for example.

The alignment light projection system 2, the movement mechanism 200, the anterior segment cameras 300, the alignment processor 2251, and the controller 210 are an example of the "alignment unit" according to the embodiments. The converter 2252A and the image tilt angle calculator 2252B are an example of the "first calculator" according to the embodiments. The tilt angle of the tomographic image is an example of the "first tilt angle" according to the embodiments. The fundus tilt angle calculator 2252C is an example of the "second tilt angle calculator" according to the embodiments. The fundus tilt angle is an example of the "second tilt angle" according to the embodiments. The anterior segment cameras 300 are an example of the "two or more imaging units" according to the embodiments. The movement target position determination unit 2251F is an example of the "position determination unit" according to the embodiments. The keratometry system 3 and the corneal shape calculator 222 are an example of the "cortical shape measurement unit" according to the embodiments. The refractometry optical system (the refractometry projection system 6 and the refractometry light reception system 7) and the eye refractive power calculator 221 are an example of the "eye refractometry unit" according to the embodiments.

<Operation Example>

The operation of the ophthalmologic apparatus 1000 according to the embodiments will be described.

Figure 15:
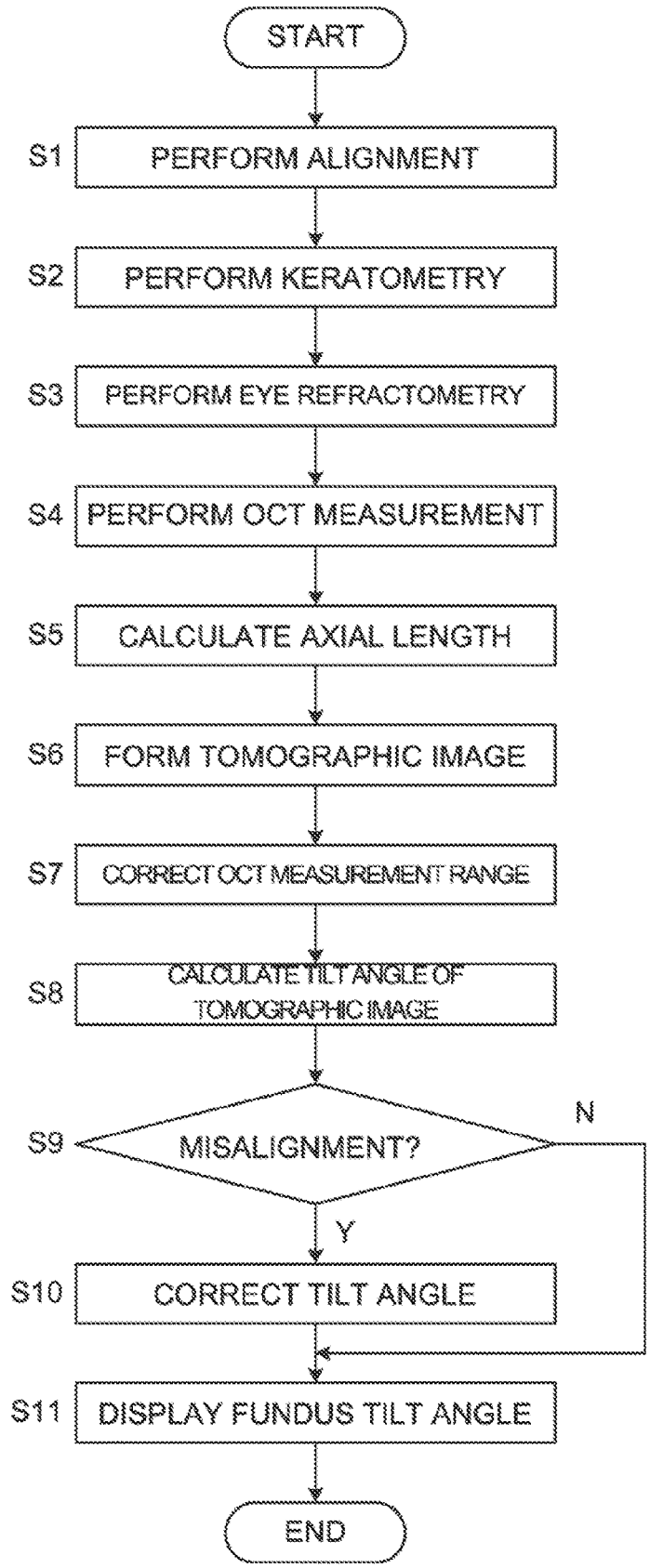
FIG. 15 is a schematic diagram representing a flow of the operation example of the ophthalmologic apparatus according to the embodiments.

FIG. 15 illustrates an example of the operation of the ophthalmologic apparatus 1000. FIG. 15 shows a flowchart of an example of the operation of the ophthalmologic apparatus 1000. The storage unit 212 stores a of computer programs for realizing the processing shown in FIG. 15. The main controller 211 operates according to the computer programs, and thereby the main controller 211 performs the processing shown in FIG. 15.

(S1: Perform Alignment)

When the examiner performs a predetermined operation on the operation unit 280 in a state Where the face of the subject is fixed to a face supporter (not shown), the ophthalmologic apparatus 1000 performs alignment.

Specifically, the main controller 211 turns on the alignment light source 21. Further, the main controller 211 controls the anterior segment cameras 300A and 300B to photograph substantially simultaneously the anterior segment of the subject's eye E onto which the alignment light emitted from the alignment light source 21 is projected. The main controller 211 controls the movement mechanism 200 based on the position of the optical system of the apparatus obtained by the optical system position obtaining unit 213 and the movement target position obtained by the alignment processor 2251 as described above, thereby the optical system shown in FIG. 1 is moved to the test position. The test position is a position where the test of the subject's eye E can be performed with sufficient accuracy.

Further, the main controller 211 moves the refractometry light source 61, the focusing lens 74, and the fixation unit 40 (liquid crystal panel 41) along the respective optical axes to the origin positions (for example, the position corresponding to 0 D).

(S2: Perform Keratometry)

Next, the main controller 211 controls the liquid crystal panel 41 to display the pattern representing the fixation target at a display position corresponding to the desired fixation position. Thereby, the subject's eye E is gazed at the desired fixation position. After that, the main controller 211 turns on the kerato-ring light source 32. When the light is emitted from the kerato-ring light source 32, a ring-shaped light beam for corneal shape measurement is projected onto the cornea Cr of the subject's eye E. The corneal shape calculator 222 applies arithmetic processing to the image acquired by the imaging element 59 to calculate the radius of the corneal curvature. Furthermore, based on calculated radius of the corneal curvature, the corneal shape calculator 222 calculates the corneal refractive power, the corneal astigmatic power, and the corneal astigmatic axis angle. The calculated corneal refractive power and the like are stored in the storage unit 212 in the controller 210.

Upon reception of an instruction from the main controller 211, an operation or instruction on the operation unit 280 by the user, the operation of the ophthalmologic apparatus 1000 proceeds to step S3.

(S3: Perform Eye Refractometry)

In the eye refractometry, the main controller 211 causes a ring-shaped measurement pattern light beam for refractometry to be projected onto the subject's eye E as described above. The ring image based on the returning light of the measurement pattern light beam from the subject's eye E is imaged on the imaging surface of the imaging element 59. The main controller 211 determines whether or not the ring image based on the returning light from the fundus Ef detected by the imaging element 59 can be acquired. For example, the main controller 211 detects a position (pixel) of the edge of the image that is formed based on the returning light detected by the imaging element 59, and determines whether or not the width (difference between outer diameter and inner diameter) of the image is equal to or more than a predetermined value. Alternatively, the main controller 11 determines whether or not the ring image can be acquired by determining whether or not a ring can be formed based on points (image) having a predetermined height (ring diameter) or more.

When it is determined that the ring image can be acquired, the eye refractive power calculator 221 analyzes the ring image based on the returning light of the measurement pattern light beam projected onto the subject's eye E by a known method, and calculates a provisional spherical power S and a provisional astigmatic power C. Based on the obtained provisional spherical power S and the obtained provisional astigmatic power C, the main controller 211 sets the refractometry light source 61, the focusing lens 74, and the fixation unit 40 (liquid crystal panel 41) to respective positions of the equivalent spherical power (S+C/2) (positions corresponding to a provisional far point). The main controller 211 moves the fixation unit 40 (liquid crystal panel 41) further to the fogging position from the position, and then controls the refractometry projection system 6 and the refractometry light reception system 7 to acquire an ring image again as the main measurement. The main controller 211 controls the eye refractive power calculator 221 to calculate a spherical power, an astigmatic power, and an astigmatic axis angle from the result of analyzing the ring image acquired in the same manner as described above and the movement amount of the focusing lens 74.

Further, the eye refractive power calculator 221 obtains a position corresponding the far point of the subject's eye E (position corresponding to the far point obtained by the main measurement) from the obtained spherical power and the obtained astigmatic power. The main controller 211 moves the liquid crystal panel 41 to the position corresponding to the obtained far point. In the controller 210, the position of the focusing lens 74, the calculated spherical power, and the like are stored in the storage unit 212. Upon reception of an instruction from the main controller 211, an operation or instruction on the operation unit 280 by the user, the operation of the ophthalmologic apparatus 1000 proceeds to step S4.

When it is determined that the ring image can not be acquired, the main controller 211 moves the refractometry light source 61 and the focusing lens 74 to the minus power side (for example, −10 D) or the plus power side (for example, +10 D) in a preset step, considering the possibility of high refractive error of the eye. The main controller 211 controls the refractometry light reception system 7 to detect the ring image at each position. If it is still determined that the ring image can not be acquired, the main controller 211 executes a predetermined measurement error process. In this case, the operation of the ophthalmologic apparatus 1000 may proceed to step S4. In the controller 210, information indicating that the result of refractometry can not be acquired is stored in the storage unit 212.

(S4: Perform OCT Measurement)

First, the main controller 211 moves the fixation unit 40 (liquid crystal panel 41) from the fogging position to the in-focus position. In some embodiments, the in-focus position is the position of the equivalent spherical power (S+C/2) specified in step S3 or a position where the focus is adjusted so that the intensity of the interference signal or the like becomes maximum with reference to the position of the equivalent spherical power (S+C/2).

Subsequently, the main controller 211 turns on the OCT light source 101 and controls the optical scanner 88 so as to scan a predetermined site (for example, a site including the macular region) of the fundus Ef with the measurement light LS.

(S5: Calculate Axial Length)

The main controller 211 controls the intraocular distance calculator 223 to calculate the axial length of the subject's eye E. The intraocular distance calculator 223 specifies a position corresponding to the corneal apex and a position corresponding to the fundus from the peak positions of the detection signal of the interference light LC acquired in step S4, and calculates the axial length from the specified positions.

(S6: Form Tomographic Image)

The main controller 211 sends the detection signal acquired by scanning with the measurement light LS in step S4 to the image forming unit 224 and controls the image forming unit 224 to form the tomographic image of the fundus Ef from the detection signal.

(S7: Correct OCT Measurement Range)

Subsequently, the main controller 211 specifies the OCT measurement range (distance in the horizontal direction of the tomographic image) as shown in FIG. 10, and controls the converter 2252A to convert the specified OCT measurement range into a value corresponding to actual dimension. The converter 2252A converts the OCT measurement range into the value corresponding to the actual dimension using the radius of the corneal curvature acquired in step S2, the eye refractive power acquired in step S3, and the axial length acquired in step S5.

(S8: Calculate Tilt Angle of Tomographic Image)

Next, the main controller 211 controls the image tilt angle calculator 2252B to calculate the tilt angle of the tomographic image formed in step S6, as shown in FIG. 10.

(S9: Misalignment?)

The main controller 211 controls the tilt angle processor 2252 to acquire misalignment amount specified by the misalignment specifying unit 2251G when the OCT measurement in step S4 is performed, and determines whether or not the eyeball optical axis is shifted or tilted with respect to the measurement optical axis.

When it is determined by the tilt angle processor 2252 that the eyeball optical axis is shifted or tilted with respect to the measurement optical axis (S9: Y), the operation of the ophthalmologic apparatus 1000 proceeds to step S10. When it is determined by the tilt angle processor 2252 that the eyeball optical axis is not shifted or tilted with respect to the measurement optical axis (S9: N), the operation of the ophthalmologic apparatus 1000 proceeds to step S11.

(S10: Correct Tilt Angle)

When it is determined that the eyeball optical axis is shifted or tilted with respect to the measurement optical axis in step S9 (S9: Y), the main controller 211 controls the fundus tilt angle calculator 2252C to correct the tilt angle of the tomographic image calculated in step S9.

That is, when it is determined that the eyeball optical axis is shifted with the measurement optical axis, the fundus tilt angle calculator 2252C obtains the fundus tilt angle g1 by correcting the tilt angle g0 of the tomographic image according to expressions (3) and (4), as described above.

Further, when it is determined that the eyeball optical axis is tilted with the measurement optical axis, the fundus tilt angle calculator 2252C obtains the fundus tilt angle g1 by correcting the tilt angle g0 of the tomographic image according to expressions (5) and (6), as described above.

Further, when it is determined that the eyeball optical axis is shifted and tilted with the measurement optical axis, the fundus tilt angle calculator 2252C obtains the fundus tilt angle g1 by correcting the tilt angle g0 of the tomographic image according to expressions (7) and (8), as described above.

(S11: Display Fundus Tilt Angle)

When it is determined that the eyeball optical axis substantially coincides with the measurement optical axis in step S9 (S9: N), the main controller 211 controls the display unit 270 to display, as the fundus tilt angle g1, the tilt angle g0 of the tomographic image obtained in step S8 without correcting the tilt angle g0.

Besides, the main controller 211 controls the display unit 270 to display the fundus tilt angle corrected in step S10. This terminates the operation of the ophthalmologic apparatus 1000 (END).

MODIFICATION EXAMPLE

First Modification Example

In the above embodiments, examples are described in which the eye refractive power is acquired by the refractometry optical system and the OCT measurement range is corrected using the acquired eye refractive power; however, they are not so limited.

For example, the eye refractive power may be specified from the position of the focusing lens 87 determined in the focus adjustment performed before the OCT measurement, and the OCT measurement range may be corrected using specified eye refractive power, as described above. In this case, the storage unit 212 stores correspondence information in which positions of the focus lens 87 are associated with eye refractive powers in advance, and the main controller 211 specifies the eve refractive power corresponding to the position of the focusing lens 87 by referring to the correspondence information. According the present modification example, the ophthalmologic apparatus 1000 does not need to have the configurations of the refractometry projection system 6 and the refractometry light reception system 7.

Figure 16:
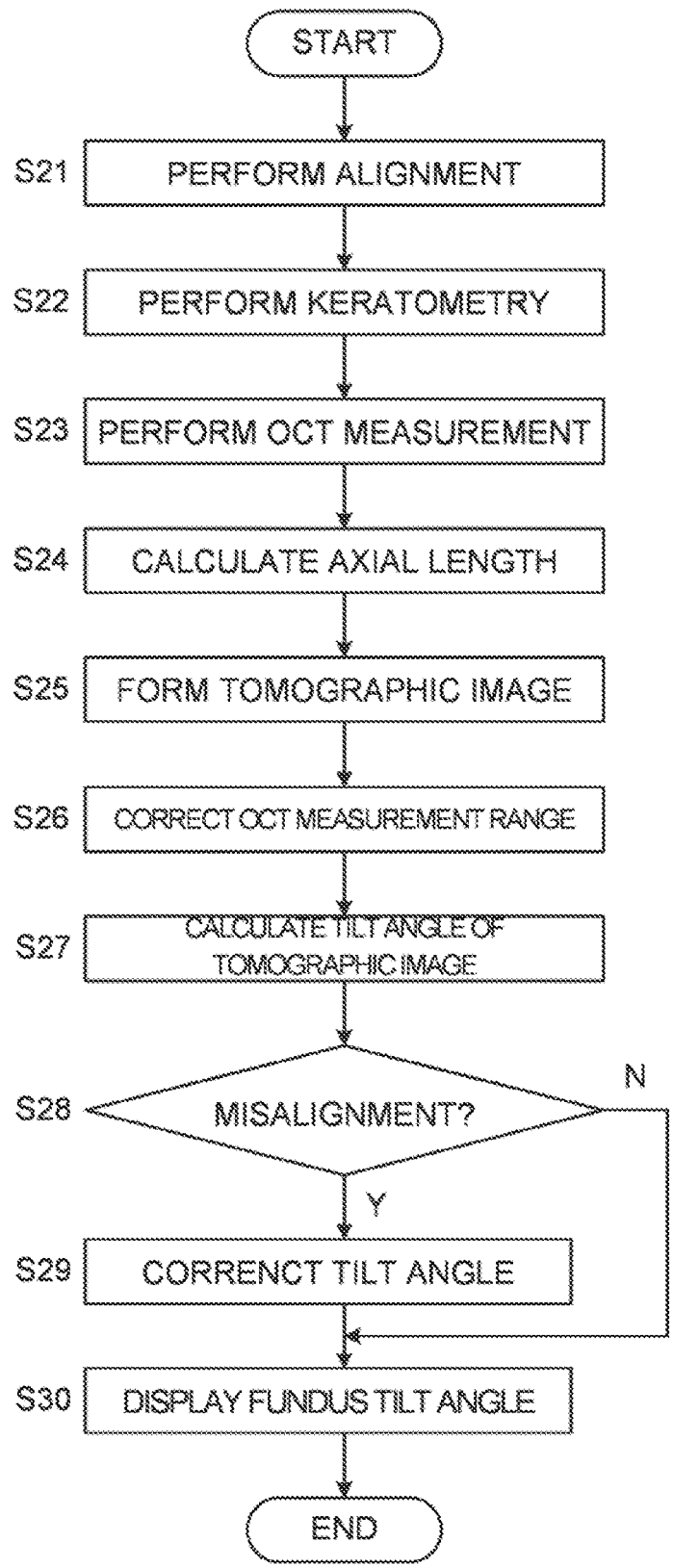
FIG. 16 is a schematic diagram representing a flow of the operation example of the ophthalmologic apparatus according to a first modification example of the embodiments.

FIG. 16 shows an example of the operation of the ophthalmologic apparatus according to the first modification example of the embodiments. FIG. 16 shows a flow chart of the example of the operation of the ophthalmologic apparatus according to the first modification example of the embodiments. The storage unit 212 stores a computer program for realizing the processing shown in FIG. 16. The main controller 211 operates according to the computer programs, and thereby main controller 211 performs the processing shown in FIG. 16.

(S21: Perform Alignment)

The ophthalmologic apparatus performs alignment in the same manner as step S1.

(S22: Perform Keratometry)

Next, the main controller 211 causes the keratometry to be performed in the same manner as step S2.

(S23: Perform OCT Measurement)

Subsequently, the main controller 211 causes the OCT measurement to be performed in the same manner as step S4. At this time, the eye refractive power of the subject's eye E is specified from the position of the focusing lens 87 determined in the focus adjustment performed before the OCT measurement.

(S24: Calculate Axial Length)

The main controller 211 controls the intraocular distance calculator 223 to calculate the axial length of the subject's eye E in the same manner as step S5.

(S25: Form Tomographic Image)

The main controller 211 controls the image forming unit 224 to form the tomographic image of the fundus Ef in the same manner as step SC.

(S26: Correct OCT Measurement Range)

Subsequently, the main controller 211 controls the converter 2252A to convert the specified OCT measurement range into the value corresponding to the actual dimension in the same manner as step S7. At this time, the converter 2252A converts the OCT measurement range into the value corresponding to the actual dimension by using the radius of the corneal curvature acquired in step S22, the eye refractive power corresponding to the position of the focusing lens 87 determined in the focus adjustment performed before the OCT measurement in step S23, and the axial length acquired in step S24. That is, the image tilt angle calculator 2252B according the first modification example converts the distance in the horizontal direction of the frame of the tomographic image into the value corresponding to the actual dimension based on the radius of the corneal curvature, the position of the focusing lens 87 on the measurement optical axis, and the axial length.

(S27: Calculate Tilt Angle of the Tomographic Image)

Next, the main controller 211 controls the image tilt angle calculator 2252B to calculate the tilt angle of the tomographic image formed in step S25, in the same manner as step S8.

(S28: Misalignment?)

The main controller 211 determines whether the eyeball optical axis is shifted or tilted with respect to the measurement optical axis in the same manner as step S9.

When it is determined by the tilt angle processor 2252 that the eyeball optical axis is shifted or tilted with respect to the measurement optical axis (S28: Y), the operation of the ophthalmologic apparatus 1000 proceeds to step S29. When it is determined by the tilt angle processor 2252 that the eyeball optical axis is not shifted or tilted with respect to the measurement optical axis (S28: N), the operation of the ophthalmologic apparatus 1000 proceeds to step S30.

(S29: Correct Tilt Angle)

When it is determined that the eyeball optical axis is shifted or tilted with respect to the measurement optical axis in step S28 (S28: Y), the main controller 211 controls the fundus tilt angle calculator 2252C to correct the tilt angle of the tomographic image calculated in step S27, in the same manner as step S10.

(S30: Display Fundus Tilt Angle)

When it is determined that the eyeball optical axis substantially coincides with the measurement optical axis in step S28 (S28: N), the main controller 211 controls the display unit 270 to display, as the fundus tilt angle, the tilt angle of the tomographic image obtained in step S27 without correcting the tilt angle of the tomographic image.

Besides, the main controller 211 controls the display unit 270 to display the fundus tilt angle corrected in step S29. This terminates the operation of the ophthalmologic apparatus according to the first modification example (END).

Second Modification Example

In the above embodiments or the first modification example, in the case that a plurality of the OCT measurements are performed on the same subject's eye for the purpose of follow-up observation, information representing a change over time of the calculated fundus tilt angle may be displayed on the display unit 270.

In the second modification example, every time the OCT measurement is performed for follow-up observation, the tilt angle processor 2252 (fundus tilt angle calculator 2252C) obtains the fundus tilt angle as described above. The main controller 211 stores the obtained fundus tilt angle in the storage unit 212 in association with information (data and time information, time information) representing performing timing of the OCT measurement (acquisition tuning of OCT data).

For example, upon reception of a predetermined operation on the operation unit 280, the main controller 211 (controller 210) controls the display unit 270 (display means) to display information representing a change over time of the fundus tilt angle based on the fundus tilt angle stored in the storage unit 212 and the information representing performing timing of the OCT measurement. In some embodiments, every time the fundus tilt angle is calculated by the fundus tilt angle calculator 2252C, the main controller 211 controls the display unit 270 to display the information representing a change over time of the fundus tilt angle reflecting the calculated fundus tilt angle.

Figure 17:
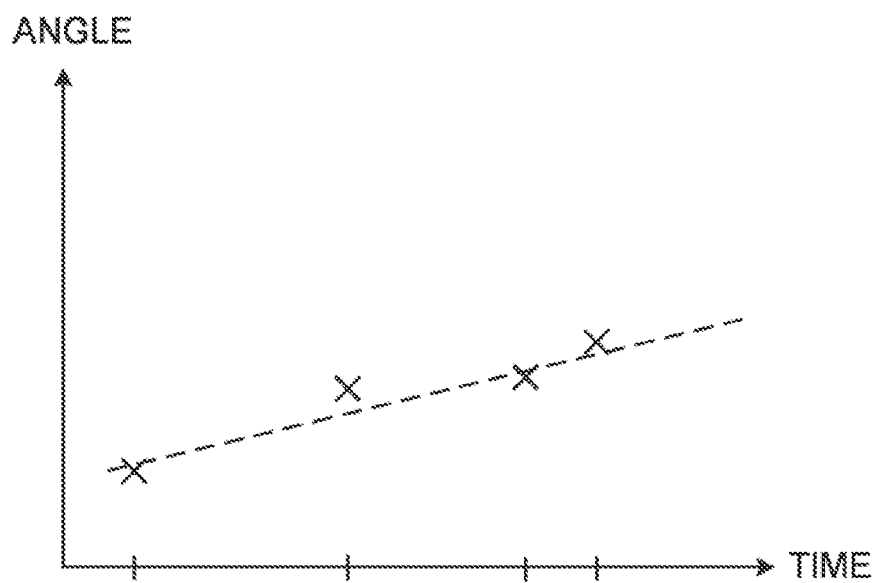
FIG. 17 is a schematic diagram for explaining an operation of the ophthalmologic apparatus according to a second modification example of the embodiments.

FIG. 17 shows a schematic diagram of an example of the information representing the change over time of the fundus tilt angle according to the second modification example of the embodiments.

FIG. 17 schematically illustrates a trend graph of the fundus tilt angle, as an example of the information representing the change over time of the fundus tilt angle. That is, in FIG. 17, the horizontal axis represents information indicating the performing timing of the OCT measurement, and the vertical axis represents the fundus tilt angle acquired by each OCT measurement.

In some embodiments, the main controller 211 controls the data processor 225 to perform regression analysis on a plurality of calculated values of the fundus tilt angle stored in the storage unit 212. The main controller 211 superimposes the regression line (or regression curve) obtained by the regression analysis by the data processor 225 on the trend graph shown in FIG. 17 and displays it. Thereby, the fundus tilt angle in the future can be estimated.

In the second modification example, the difference between the calculated fundus tilt angle and the previously calculated fundus tilt angle may be displayed on the display unit 270 in chronological order.

As explained above, according to the second modification example, the change over time of the fundus tilt angle is visualized. Thereby, it is possible to easily grasp how the high myopia and the like is going and this method can be used for screening of advanced myopia (especially for children).

Third Modification Example

In the above embodiments or the modification examples thereof, in order to easily grasp the degree of tilt of the fundus of the subject's eye, information representing a reference range of the fundus tilt angle may be superimposed on the tomographic image of the fundus and displayed it on the display unit 270.

In the third modification example, a standard tilt angle of the fundus is specified from standard data, and information representing the reference range of the fundus tilt angle with reference to the specified standard tilt angle is calculated in advance. The standard data is normal eye data (normative data) statistically derived from measured data (or calculated data) of the tilt angle of the fundus of the of many normal eyes.

The main controller 211 (controller 210) controls the display unit 270 to display the tomographic image formed by the image forming unit 224. In some embodiments, the data processor 225 corrects the tilt angle of the tomographic image so that the fundus tilt angle calculated by the fundus tilt angle calculator 2252C becomes 0 degree (the fundus is in the horizontal direction). The main controller 211 controls the display unit 270 to display the tomographic whose tilt has been corrected based on the calculated fundus tilt angle. The main controller 211 controls the display unit 270 (display means) to display information representing the calculated reference range of the tilt angle of the fundus in advance on the tomographic image. The main controller 211 is capable of superimposing the information representing the reference range of the tilt angle of the fundus on the tomographic image with reference to the macular region specified in the tomographic image and displaying it.

Figure 18:
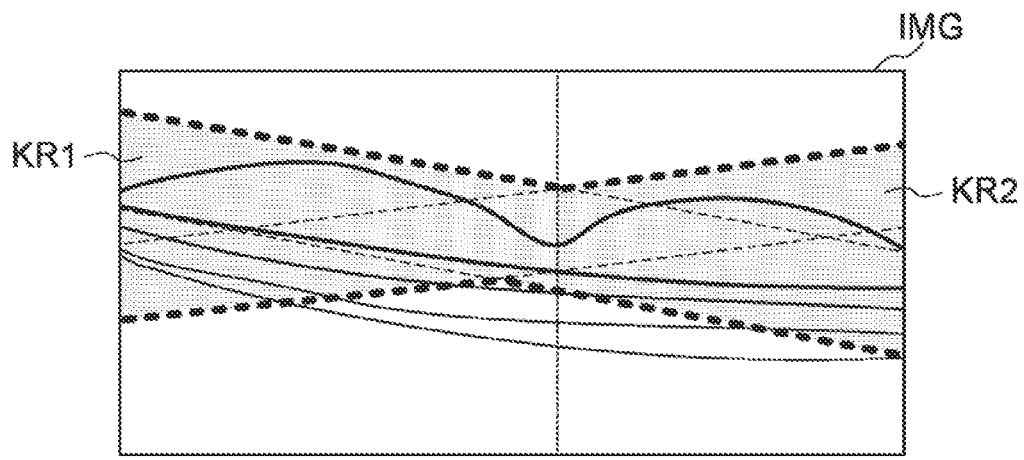
FIG. 18 is a schematic diagram for explaining an operation of the ophthalmologic apparatus according to a third modification example of the embodiments.

FIG. 18 shows a schematic diagram of an example of the information representing the standard tilt angle of the fundus superimposed on the tomographic image according to the third modification example of the embodiments.

In FIG. 18, the reference range KR1 descending to the right is depicted in the region on the left side with respect to the macular region, and the reference range KR2 descending to the left is depicted in the region on the right side with respect to the macular region. By superimposing and displaying the reference ranges KR1 and KR2 on the tomographic image, the degree of the tilt of the fundus of the subject's eye can be easily grasped. The reference range can be an allowable range for determining whether or not the calculated fundus tilt angle falls within the standard fundus tilt angle.

For example, the main controller 211 may control the data processor 225 to specify a predetermined layer region (for example, the inner nuclear layer or the retinal pigment epithelium layer) of the fundus in the tomographic image and may determine whether or not the specified predetermined layer region is included in the reference regions KR1 and KR2. The main controller 211 is capable of displaying the result of determination by the data processor 225 on the display unit 270. Thereby, alerts for high myopia and other eye diseases due to tilt of the fundus can be output.

In the third modification example, the deviation of the calculated fundus tilt angle with respect to the standard fundus tilt angle may be displayed on the display unit 270.

[Actions and Effects]

Described below are the actions and effects of the ophthalmologic apparatus according to the embodiments.

An ophthalmologic apparatus (1000) according to sonic embodiments includes an OCT optical system (8), an alignment unit (alignment light projection system 2, movement mechanism 200, anterior segment cameras 300, alignment processor 2251, and controller 210), an image forming unit (224), a first calculator (converter 2252A and image tilt angle calculator 2252B), and a second calculator (fundus tilt angle calculator 2252C). The OCT optical system acquires OCT data of a fundus (Ef) of a subject's eye (E) by projecting measurement light (LS) onto the fundus. The alignment unit performs alignment of the OCT optical system with reference to a predetermined site of the subject's eye. The image forming unit forms a tomographic image of the fundus based on the OCT data acquired by the OCT optical system which has been aligned by the alignment unit. The first calculator calculates a first tilt angle (g0) of the tomographic image. The second calculator calculates a second tilt angle (g1) of the fundus by correcting the first tilt angle based on alignment result of the OCT optical system with respect to the predetermined site by the alignment unit.

According to such a configuration, the second tilt angle of the fundus is acquired by correcting the first tilt angle of the tomographic image based on the result of alignment. Thereby, the tilt angle of the fundus of the subject's eye can be measured with high accuracy. Therefore, it is possible to specify whether the tilt of the fundus in the tomographic image is caused by the state of alignment or truly due to the deformation of the posterior of the eyeball.

The ophthalmologic apparatus according to some embodiments further includes a misalignment amount specifying unit (2251G) that specifies a misalignment amount between a measurement optical axis of the OCT optical system (optical axis of the objective lens 51) which has been aligned by the alignment unit and an eyeball optical axis of the subject's eye, and the second calculator calculates the second tilt angle based on the misalignment amount.

According to such a configuration, the second tilt angle is calculated from the misalignment amount between the measurement optical axis of the OCT optical system and the eyeball optical axis of the subject's eye. Thereby, the tilt angle of the fundus with respect to the eyeball optical axis can be measured with high accuracy.

In the ophthalmologic apparatus according to some embodiments, the second calculator outputs the first tilt angle as the second tilt angle when the measurement optical axis substantially coincides with the eyeball optical axis.

According to such a configuration, even when it is determined that there is no deviation between the measurement optical axis of the OCT optical system and the eyeball optical axis of the subject's eye, the tilt angle of the fundus with respect to the eyeball optical axis can be measured with high accuracy.

In the ophthalmologic apparatus according to some embodiments, the misalignment amount specifying unit specifies, as a shift amount, a displacement amount of the eyeball optical axis with respect to the measurement optical axis in a direction intersecting (orthogonal to) the measurement optical axis, and the second calculator calculates the second tilt angle by correcting the first tilt angle based on the shift amount, when the eyeball optical axis is shifted with respect to the measurement optical axis.

According to such a configuration, the shift amount of the eyeball optical axis with respect to the measurement optical axis is specified and the second tilt angle is calculated by correcting the first tilt angle based on the specified shift amount. Thereby, even when the eyeball is shifted with respect to the measurement optical axis, the tilt angle of the fundus with respect to the eyeball optical axis can be measured with high accuracy.

In the ophthalmologic apparatus according to some embodiments, the second calculator calculates the second tilt angle by correcting the first tilt a according to a linear expression with the shift amount as variable.

According to such a configuration, even when the eyeball optical axis is shifted with respect to the measurement optical axis, the tilt angle of the fundus with respect to the eyeball optical axis can be measured with high accuracy by a simple processing using a schematic eye data.

In the ophthalmologic apparatus according to some embodiments, the misalignment amount specifying unit specifies, as a tilt amount, an angle formed by the eyeball optical axis with respect to the measurement optical axis, and the second calculator calculates the second tilt angle by correcting the first tilt angle based on the tilt amount, when the eyeball optical axis is tilted with respect to the measurement optical axis.

According to such a configuration, the tilt amount of the eyeball optical axis with respect to the measurement optical axis is specified and the second tilt angle is calculated by correcting the first tilt angle based on the specified tilt amount. Thereby, even when the eyeball is tilted with respect to the measurement optical axis, the tilt angle of the fundus with respect to the eyeball optical axis can be measured with high accuracy.

In the ophthalmologic apparatus according to some embodiments, the second calculator calculates the second tilt angle by correcting the first tilt angle according to a linear expression with the tilt amount as variable.

According to such a configuration, even when the eyeball optical axis is tilted with respect to the measurement optical axis, the tilt angle of the fundus with respect to the eyeball optical axis can be measured with high accuracy by a simple processing using a schematic eye data.

In the ophthalmologic apparatus according to some embodiments, the misalignment amount specifying unit specifies, as a shift amount, a displacement amount of the eyeball optical axis with respect to the measurement optical axis in a direction intersecting (orthogonal to) the measurement optical axis, and specifies, as a tilt amount, an angle formed by the eyeball optical axis with respect to the measurement optical axis, and the second calculator calculates the second tilt angle by correcting the first tilt angle based on the shift amount and the tilt amount, when the eyeball optical axis is shifted and tilted with respect to the measurement optical axis.

According to such a configuration, the shift amount and the tilt amount of the eyeball optical axis with respect to the measurement optical axis are specified and the second tilt angle is calculated by correcting the first tilt angle based on the specified shift amount and the specified tilt amount. Thereby, even when the eyeball is shifted and tilted with respect to the measurement optical axis, the tilt angle of the fundus with respect to the eyeball optical axis can be measured with high accuracy.

In the ophthalmologic apparatus according to some embodiments, the second calculator calculates the second tilt angle by correcting the first tilt angle according to a combining expression obtained by linearly combined a linear expression with the shift amount as variable and a linear expression with the tilt amount as variable.

According to such a configuration, even when the eyeball optical axis is shifted and tilted with respect to the measurement optical axis, the tilt angle of the fundus with respect to the eyeball optical axis can be measured with high accuracy by a simple processing.

The ophthalmologic apparatus according to some embodiments further includes a fixation projection system (4) that projects a fixation flux onto the fundus in acquiring the OCT data, and the eyeball optical axis is a visual axis.

According to such a configuration, the tilt angle of the fundus with respect to the visual axis of the subject's eye can be measured with high accuracy.

In the ophthalmologic apparatus according to some embodiments, the alignment unit includes an alignment light projection system (2) that projects alignment light onto the subject's eye, a movement mechanism (200) that moves relatively the subject's eye and the OCT optical system, two or more imaging units (anterior segment cameras 300) that photographs an anterior segment of the subject's eye, onto which the alignment light is being projected, from different directions, and a position determination unit (movement target position determination unit 2251F) that specifies a first position of a reflection image (Purkinje image) of a cornea by the alignment light and a second position of the predetermined site by analyzing two or more photographic images obtained by the two or more imaging units, and to determine a movement target position of the OCT optical system based on the first position and the second position.

According to such a configuration, the ophthalmologic apparatus capable of measuring the tilt angle of the fundus with respect to the eyeball of the subject's eye with high accuracy by highly accurately specifying the position of the reflection image of the cornea and the position of the predetermined site of the subject's eye with a wide alignment possible range (dynamic range) can be provided.

In the ophthalmologic apparatus according to some embodiments, when a value, which is obtained by converting a difference of a distance in a vertical direction between an image region of a site corresponding to a predetermined layer region of the fundus at a right end of a frame of the tomographic image and an image region of the site at a left end of the frame into a value corresponding to an actual dimension, is d and a value, which is obtained by converting a distance in a horizontal direction of the frame of the tomographic image into a value corresponding to an actual dimension, is c, the first calculator calculates the first tilt angle by obtaining arctan (|d|/c).

According to such a configuration, the first tilt angle can be calculated with a simple processing.

The ophthalmologic apparatus according to some embodiments further includes a corneal shape measurement unit (keratometry system 3, corneal shape calculator 222) that performs measurement of at least a corneal curvature radius of the subject's eye, an eye refractometry unit (refractometry projection system 6, refractometry light reception system 7, and eye refractive power calculator 221) that performs measurement of an eye refractive power of the subject's eye, and an intraocular distance calculator (223) that calculates an axial length of the subject's eye based on the OCT data, and the first calculator converts the distance of the frame of the tomographic image in the horizontal direction into the actual dimension based on the corneal curvature radius, the eye refractive power, and the axial length.

According to such a configuration, since the first tilt angle reflecting the optical characteristic of the eyeball of the subject's eye can be calculated, the ophthalmologic apparatus capable of measuring the tilt angle of the fundus with higher accuracy can be provided.

The ophthalmologic apparatus according to sonic embodiments further includes a corneal shape measurement unit (keratometry system 3, corneal shape calculator 222) that performs measurement of at least a cortical curvature radius of the subject's eye, and an intraocular distance calculator (223) that calculates an axial length of the subject's eye based on the OCT data, and the OCT optical system includes a focusing lens (87) that is movable along the measurement optical axis, and the first calculator converts the distance of the frame of the tomographic image in the horizontal direction into the actual dimension based on the corneal curvature radius, a position of the focusing lens on the measurement optical axis, and the axial length.

According to such a configuration, even when the eye refractometry unit is no provided, the ophthalmologic apparatus with a simple configuration, which is capable of measuring the tilt angle of the fundus with higher accuracy by calculating the first tilt angle reflecting the optical characteristic of the eyeball of the subject's eye, can be provided.

In the ophthalmologic apparatus according to some embodiments, the first calculator converts the difference of the distance into the actual dimension by multiplying the difference of the distance by a predetermined pixel spacing value.

According to such a configuration, the first tilt angle can be calculated with a simple processing.

The ophthalmologic apparatus according to some embodiments further includes a storage unit (212) that stores the second tilt angle calculated by the second calculator in association with information representing acquisition tuning of the OCT data, and a controller (210) that controls a display means (display unit 270) to display information representing a change over time of the second tilt angle based on the second tilt angle and the information representing the acquisition timing stored in the storage unit.

According to such a configuration, the change over time of the fundus tilt angle is visualized. Thereby, it is possible to easily grasp how the high myopia and the like is going and this method can be used for screening of advanced myopia (especially for children).

The ophthalmologic apparatus according to some embodiments further includes a controller (210) that controls a display means (display unit 270) to display information representing a reference range of a tilt angle of the fundus so as to be superimposed on the tomographic image formed by the image forming unit.

According such a configuration, the degree of tilt of the fundus of the subject's eye can be easily grasped.

<Others>

In the above embodiments or the modification examples thereof, the case has been described in which the eye refractive power is acquired by projecting light onto the subject's eye; however, the configuration of the ophthalmologic apparatus according to the embodiments is not limited thereto. The ophthalmologic apparatus according to the embodiments may acquire the eye refractive power based on the wavefront aberration acquired by using a known wavefront sensor.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus comprising:
    an OCT optical system configured to acquire OCT data of a fundus of a subject's eye by projecting measurement light onto the fundus;
    an alignment unit configured to perform alignment of the OCT optical system with reference to a predetermined site of the subject's eye;
    an image forming unit configured to form a tomographic image of the fundus based on the OCT data acquired by the OCT optical system which has been aligned by the alignment unit;
    a first calculator configured to calculate a first tilt angle of the tomographic image; and
    a second calculator configured to calculate a second tilt angle of the fundus by correcting the first tilt angle based on alignment result of the OCT optical system with respect to the predetermined site by the alignment unit.

2. The ophthalmologic apparatus of claim 1, further comprising:
    a misalignment amount specifying unit configured to specify a misalignment amount between a measurement optical axis of the OCT optical system which has been aligned by the alignment unit and an eyeball optical axis of the subject's eye, wherein
    the second calculator calculates the second tilt angle based on the misalignment amount.

3. The ophthalmologic apparatus of claim 2, wherein
    the second calculator outputs the first tilt angle as the second tilt angle when the measurement optical axis substantially coincides with the eyeball optical axis.

4. The ophthalmologic apparatus of claim 2, wherein
    the misalignment amount specifying unit specifies, as a shift amount, a displacement amount of the eyeball optical axis with respect to the measurement optical axis in a direction intersecting the measurement optical axis, and
    the second calculator calculates the second tilt angle by correcting the first tilt angle based on the shift amount, when the eyeball optical axis is shifted with respect to the measurement optical axis.

5. The ophthalmologic apparatus of claim 4, wherein
    the second calculator calculates the second tilt angle by correcting the first tilt angle according to a linear expression with the shift amount as variable.

6. The ophthalmologic apparatus of claim 2, wherein
    the misalignment amount specifying unit specifies, as a tilt amount, an angle formed by the eyeball optical axis with respect to the measurement optical axis, and
    the second calculator calculates the second tilt angle by correcting the first tilt angle based on the tilt amount, when the eyeball optical axis is tilted with respect to the measurement optical axis.

7. The ophthalmologic apparatus of claim 6, wherein
    the second calculator calculates the second tilt angle by correcting the first tilt angle according to a linear expression with the tilt amount as variable.

8. The ophthalmologic apparatus of claim 2, wherein
    the misalignment amount specifying unit specifies, as a shift amount, a displacement amount of the eyeball optical axis with respect to the measurement optical axis in a direction intersecting the measurement optical axis, and specifies, as a tilt amount, an angle formed by the eyeball optical axis with respect to the measurement optical axis, and
    the second calculator calculates the second tilt angle by correcting the first tilt angle based on the shift amount and the tilt amount, when the eyeball optical axis is shifted and tilted with respect to the measurement optical axis.

9. The ophthalmologic apparatus of claim 8, wherein
the second calculator calculates the second tilt angle by correcting the first tilt angle according to a combining expression obtained by linearly combined a linear expression with the shift amount as variable and a linear expression with the tilt amount as variable.

10. The ophthalmologic apparatus of claim 2, further comprising:
a fixation projection system configured to project a fixation flux onto the fundus in acquiring the OCT data, wherein
the eyeball optical axis is a visual axis.

11. The ophthalmologic apparatus of claim 1, wherein the alignment unit comprises:
an alignment light projection system configured to project alignment light onto the subject's eye;
a movement mechanism configured to move relatively e subject's eye and the OCT optical system;
two or more imaging units configured to photograph an anterior segment of the subject's eye, onto which the alignment light is being projected, from different directions; and
a position determination unit configured to specify a first position of a reflection image of a cornea by the alignment light and a second position of the predetermined site by analyzing two or more photographic images obtained by the two or more imaging units, and to determine a movement target position of the OCT optical system based on the first position and the second position.

12. The ophthalmologic apparatus of claim 1, wherein
when a value, which is obtained by converting a difference of a distance in a vertical direction between an image region of a site corresponding to a predetermined layer region of the fundus at a right end of a frame of the tomographic image and an image region of the site at a left end of the frame into a value corresponding to an actual dimension, is d and a value, which is obtained by converting a distance in a horizontal direction of the frame of the tomographic image into a value corresponding to an actual dimension, is c,
the first calculator calculates the first tilt angle by obtaining arctan ($|d|/c$).

13. The ophthalmologic apparatus of claim 12, further comprising:
a corneal shape measurement unit configured to perform measurement of at least a corneal curvature radius of the subject's eye;

an eye refractometry unit configured to perform measurement of an eye refractive power of the subject's eye; and
an intraocular distance calculator configured to calculate an axial length of the subject's eye based on the OCT data, wherein
the first calculator converts the distance of the frame of the tomographic image in the horizontal direction into the actual dimension based on the corneal curvature radius, the eye refractive power, and the axial length.

14. The ophthalmologic apparatus of claim 12, further comprising:
a corneal shape measurement unit configured to perform measurement of at least a corneal curvature radius of the subject's eye; and
an intraocular distance calculator configured to calculate an axial length of the subject's eye based on the OCT data, wherein
the OCT optical system includes a focusing lens that is movable along the measurement optical axis, and
the first calculator converts the distance of the frame of the tomographic image in the horizontal direction into the actual dimension based on the corneal curvature radius, a position of the focusing lens on the measurement optical axis, and the axial length.

15. The ophthalmologic apparatus of claim 12, wherein
the first calculator converts the difference of the distance into the actual dimension by multiplying the difference of the distance by a predetermined pixel spacing value.

16. The ophthalmologic apparatus of claim 1, further comprising:
a storage unit that stores the second tilt angle calculated by the second calculator in association with information representing acquisition timing of the OCT data; and
a controller that controls a display means to display information representing a change over time of the second tilt angle based on the second tilt angle and the information representing the acquisition timing stored in the storage unit.

17. The ophthalmologic apparatus of claim 1, further comprising:
a controller that controls a display means to display information representing a reference range of a tilt angle of the fundus so as to be superimposed on the tomographic image formed by the image forming unit.

* * * * *